(12) United States Patent
Seitz et al.

(10) Patent No.: US 10,857,368 B2
(45) Date of Patent: Dec. 8, 2020

(54) FLEXIBLE HERMETIC MEMBRANES WITH ELECTRICALLY CONDUCTING VIAS

(71) Applicant: Greatbatch Ltd., Clarence, NY (US)

(72) Inventors: Keith W. Seitz, Clarence Center, NY (US); Xiaohong Tang, Williamsville, NY (US); William C. Thiebolt, North Tonawanda, NY (US); Jonathan Calamel, Williamsville, NY (US); Thomas Shi, Williamsville, NY (US); Thomas Marzano, East Amherst, NY (US)

(73) Assignee: Greatbatch Ltd., Clarence, NY (US)

(*) Notice: Subject to any disclaimer, the term of this patent is extended or adjusted under 35 U.S.C. 154(b) by 340 days.

(21) Appl. No.: 15/936,495

(22) Filed: Mar. 27, 2018

(65) Prior Publication Data

US 2018/0272137 A1    Sep. 27, 2018

Related U.S. Application Data

(60) Provisional application No. 62/476,895, filed on Mar. 27, 2017.

(51) Int. Cl.
*A61N 1/375*    (2006.01)
*H05K 5/00*    (2006.01)
(Continued)

(52) U.S. Cl.
CPC .............. *A61N 1/3754* (2013.01); *C03C 8/14* (2013.01); *H01L 23/10* (2013.01); *H01L 23/15* (2013.01);
(Continued)

(58) Field of Classification Search
CPC .. H02G 3/22; H02G 3/24; H02G 3/26; H02G 15/007; H02G 15/013; H02G 15/04;
(Continued)

(56) References Cited

U.S. PATENT DOCUMENTS

| 4,420,652 A | 12/1983 | Ikeno et al. |
| 5,434,358 A | 7/1995 | Glahn et al. |

(Continued)

FOREIGN PATENT DOCUMENTS

| EP | 2617461 A1 | 7/2013 |
| WO | 2011025667 | 3/2011 |

OTHER PUBLICATIONS

EnrG Incorporated—Thin E-Strate Material Properties, Data Sheet dated 2015.
(Continued)

*Primary Examiner* — Angel R Estrada
(74) *Attorney, Agent, or Firm* — Michael F. Scalise

(57) ABSTRACT

Disclosed herein are electrically conductive and hermetic vias disposed within an insulator substrate of a feedthrough assembly and methods for making and using the same. Such aspects of the present invention consequently provide for the miniaturization of feedthrough assemblies inasmuch as the feedthrough components of the present invention are capable of supporting very small and hermetic conductively filled via holes in the absence of additional components, such as, for example, terminal pins, leadwires, and the like.

33 Claims, 3 Drawing Sheets

(51) Int. Cl.
*H05K 1/03* (2006.01)
*H05K 3/00* (2006.01)
*H01L 23/15* (2006.01)
*C03C 8/14* (2006.01)
*H01L 23/00* (2006.01)
*H01L 23/10* (2006.01)

(52) U.S. Cl.
CPC ............ *H01L 24/26* (2013.01); *H05K 1/0306* (2013.01); *H05K 3/0047* (2013.01); *H05K 5/0095* (2013.01); *C04B 2237/343* (2013.01); *C04B 2237/348* (2013.01); *C04B 2237/361* (2013.01); *C04B 2237/363* (2013.01); *C04B 2237/365* (2013.01); *C04B 2237/403* (2013.01); *C04B 2237/408* (2013.01); *H01L 2924/0104* (2013.01); *H01L 2924/01006* (2013.01); *H01L 2924/01022* (2013.01); *H01L 2924/01029* (2013.01); *H01L 2924/01041* (2013.01); *H01L 2924/01042* (2013.01); *H01L 2924/01044* (2013.01); *H01L 2924/01046* (2013.01); *H01L 2924/01047* (2013.01); *H01L 2924/01073* (2013.01); *H01L 2924/01077* (2013.01); *H01L 2924/01078* (2013.01); *H01L 2924/01079* (2013.01); *H01L 2924/09701* (2013.01)

(58) Field of Classification Search
CPC ............ H01G 4/35; H01G 4/38; H01G 4/224; H01G 4/228; H01G 4/002; A61N 1/375; A61N 1/3754; A61N 1/3752; C03C 8/14; C04B 2237/343; C04B 2237/348; C04B 2237/361; C04B 2237/363; C04B 2237/365; C04B 2237/403; C04B 2237/408; H01L 2924/01006; H01L 2924/01022; H01L 2924/01029; H01L 2924/0104; H01L 2924/01041; H01L 2924/01042; H01L 2924/01044; H01L 2924/01046; H01L 2924/01047; H01L 2924/01073; H01L 2924/01077; H01L 2924/01078; H01L 2924/01079; H01L 2924/09701; H01L 23/10; H01L 23/15; H01L 24/26; H05K 1/0306; H05K 3/0047; H05K 5/0095
USPC ......... 174/650, 152 GM, 50.61, 50.5, 50.55, 174/50.63, 520, 521; 361/302, 306.2, 361/328, 329, 306.1, 320, 321.1, 306.3; 607/36, 37, 5, 116; 439/935, 926, 587; 427/2.1; 156/250
See application file for complete search history.

(56) References Cited

U.S. PATENT DOCUMENTS

| | | |
|---|---|---|
| 5,620,476 A | 4/1997 | Truex et al. |
| 5,683,435 A | 11/1997 | Truex et al. |
| 5,750,926 A | 5/1998 | Schulman et al. |
| 5,782,891 A | 7/1998 | Hassler et al. |
| 5,973,906 A | 10/1999 | Stevenson et al. |
| 7,064,270 B2 * | 6/2006 | Marshall ............... A61N 1/3754 174/152 GM |
| 7,480,988 B2 | 1/2009 | Ok et al. |
| 7,957,806 B2 * | 6/2011 | Stevenson ............ H03H 1/0007 607/36 |
| 8,642,887 B1 | 2/2014 | Li et al. |
| 8,653,384 B2 * | 2/2014 | Tang ..................... H01G 4/005 174/650 |
| 8,698,006 B2 | 4/2014 | Kimock et al. |
| 8,763,245 B1 | 7/2014 | Lucisano et al. |
| 8,855,768 B1 * | 10/2014 | Johnson ............... A61N 1/3718 607/36 |
| 9,742,178 B2 * | 8/2017 | Thom ..................... H02G 3/22 |
| 2005/0007718 A1 | 1/2005 | Stevenson et al. |
| 2016/0287882 A1 | 10/2016 | Karst et al. |
| 2016/0311720 A1 | 10/2016 | Suffner |

OTHER PUBLICATIONS

Heiroth, "Pulsed Laser Deposition of Functional Electroceramic Thin Films for Micro Solid Oxide Fuel Cell Applications", Publication date: 2010.

Rogers, et al., "Direct Observations of Electrochemical Reactions within Au-YSZ Thin Films via Absorption Shifts in the Au Nanoparticle Surface Plasmon Resonance", J. Phys. Chem C 2008, 112, 6749-6757, Published on Web Apr. 10, 2008.

Schlichting, et al., "Thermal Conductivity of Dense and Porous Yttria-Stabilized Zirconia", Journal of Materials Science 36 (2010) 3003-3010.

Sirinakis, et al., "Development and Characterization of Au-YSZ Surface Plasmon Resonance Based Sensing Materials: High Temperature Detection of CO", J. Phys. Chem B 2006, 110, 13508-13511, published on the Web Jun. 17, 2006.

Smeacetto, et al., "Glass and Composite seals for the Joining of YSZ to Metallic Interconnect in Solid Oxide Fuel Cells", Journal of the European Ceramic Society 28, 2008, pp. 611-616.

Zhao, et al., "Thermal and Electrical Characterizations of Ultra-Thin Flexible 3YSZ Ceramic for Electronic Packaging Applications", International Symposium on Microelectronics. 2016. 000391-000396.

Extended European Search, Application No. 18164307.3, dated Jun. 29, 2018.

* cited by examiner

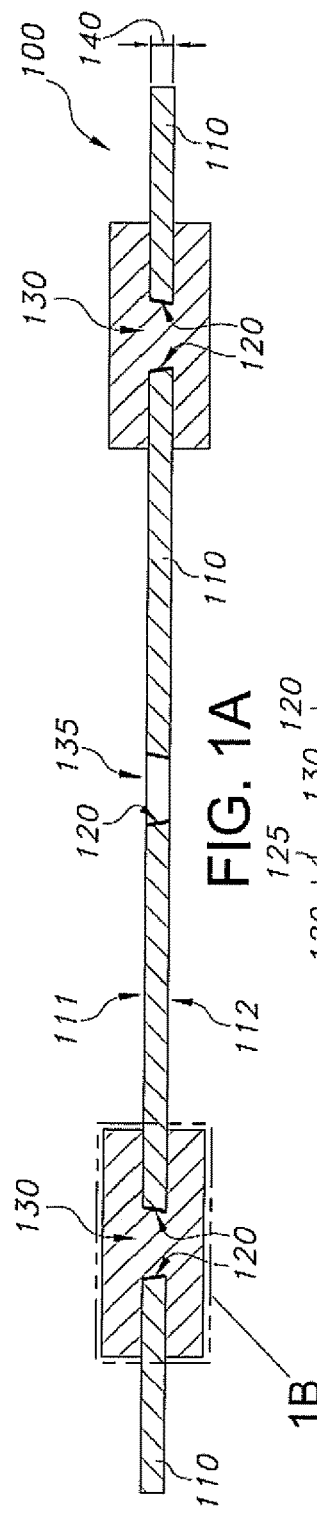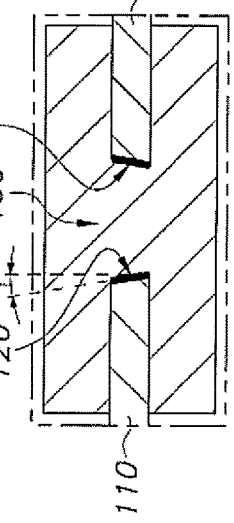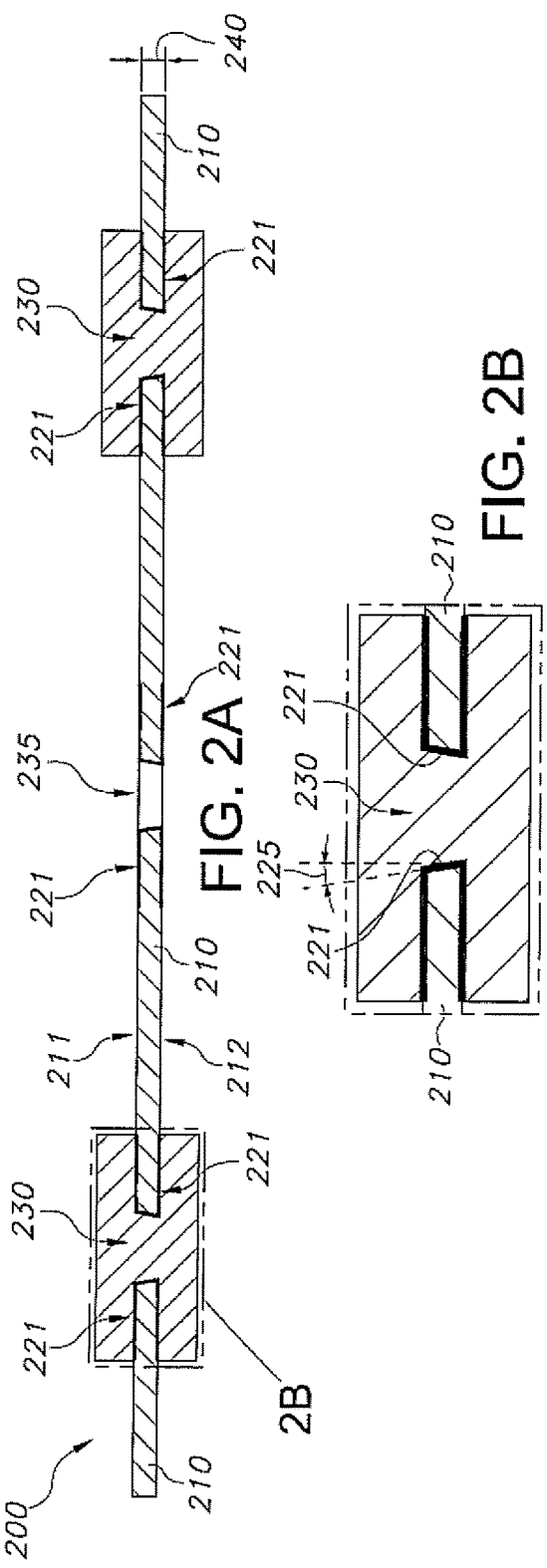

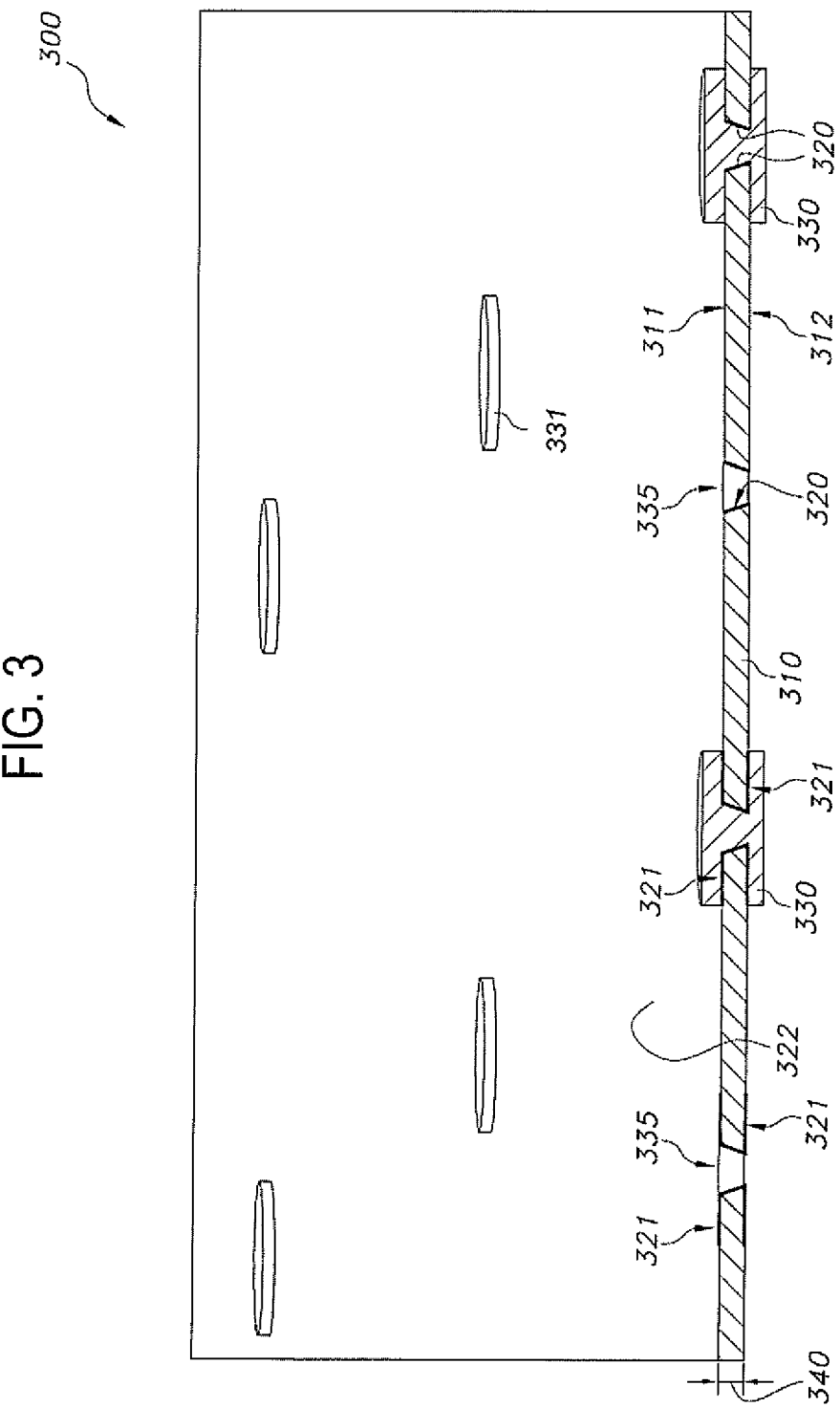

FLEXIBLE HERMETIC MEMBRANES WITH ELECTRICALLY CONDUCTING VIAS

CROSS-REFERENCE TO RELATED APPLICATIONS

This application claims priority to U.S. Provisional Patent Application Ser. No. 62/476,895 "Biocompatible Zirconia and YSZ (3 Mol %) with Hermetic Via Used for Feedthroughs," which was filed on Mar. 27, 2017, the entire contents of which are hereby incorporated by reference in its entirety.

FIELD OF THE INVENTION

The present disclosure relates generally to feedthrough assemblies. More particularly, the present invention relates to biocompatible feedthrough assemblies having ultra-thin flexible insulator substrates that possess electrically conductive hermetic vias.

BACKGROUND OF THE INVENTION

The following description is provided to assist the understanding of the reader. None of the information provided or references cited is admitted to be prior art.

Implantable medical devices are becoming increasingly smaller and more complex. And, while such diminishing confines impart an evolving framework for the design and manufacture of device components, it is nevertheless imperative that the structural and functional integrity of the devices be maintained. In concert with improvements concerning design structure, advances in biocompatibility and materials selection for implantable medical devices must similarly progress at least insofar as device miniaturization and an expanding field-of-use profile with respect to such implantable devises may not be realized pursuant to the status quo.

As integral components of implantable medical devices, feedthrough assemblies typically function as electrical interfaces that conductively connect circuit components on either side of a barrier, which, in many instances, must be hermetically sealed to ensure extended operation in corrosive environments, e.g., when implanted within the oxidative milieu of a patient's body. Within the purview of biocompatibility, in this regard, such feedthrough assemblies are typified by an electrochemical profile that remains stable with respect to the varying conditions and electrical signals that may be present on either side of a hermetic junction that it functions to maintain.

The external housing of an implantable medical device, moreover, ultimately provides the framework for supporting the feedthrough assembly. In addition to the housing, a feedthrough assembly typically entails, e.g., a ferrule hermetically contacting a substrate material that may possesses one or more interconnects or via holes extending through the substrate, which coterminously functions as an insulator with respect to a conductor, e.g., a leadwire, tube, pin, conductive paste, etc., residing in, and extending through, an insulator via hole, and consequently the feedthrough apparatus itself. The resulting feedthrough passage is therefore electrically conductive and hermetic.

Hermeticity of the feedthrough junctions are critical not only to the ultimate functionality of the medical device, but also to the health and safety of the patient harboring such a device, i.e., where any outflow of electrolytic or other device fluid would be detrimental to the patient's health. Along the same lines, it is equally important that the hermeticity of the conductive vias be established and maintained, i.e., not only for the reasons discussed above, but to further maintain and preserve the integrity of the conductive pathway, while also protecting against any ingress of corrosive bodily fluids that may be deleterious to the sensitive electronics within an implantable systems. Indeed, body fluid ingress has been identified as a compromising factor with respect to electrical circuitry and power source malfunction to this end.

Accordingly, in conjunction with a judicious materials selection process, the design and manufacture of hermetically sealed conductive feedthrough pathways, in this regard, must be carefully prescribed. And, insofar as feedthrough assemblies impart the conductive *nexus* that affords electrical communication between the internal circuitry of an implantable device and an external device environment, i.e., inside the body of a patient while also establishing the hermetic junctions residing at such an interface it is essential to ensure that adaptations concerning improvements in feedthrough efficacy and stability, as well as miniaturization of the same, do not relinquish device durability and/or reliability.

Along these lines, conductively filled hermetic vias, which do not possess extraneous terminal pins, leadwires, and the like, provide a suitable conduit for the adaptation of implantable devices, and their component features, to miniaturized configurations at least to the extent that component feedthrough volume is reduced without sacrificing conductivity, hermeticity and/or biocompatibility. As such, provided herein are hermetic feedthrough assemblies including thin flexible substrate insulators, which possess electrically conductive hermetic vias, that function as mechanical and electrical interfaces between the sensitive internal circuitry of an implantable medical device and the corrosive external body tissue environment, while contemporaneously maintaining an insulative conductive pathway.

SUMMARY

In one aspect, the present disclosure is directed to a feedthrough assembly, entailing: (a) a ferrule having an electrically conductive material, the ferrule entailing a ferrule opening, where the ferrule is configured to be attachable to an opening in a housing of a medical device, (b) an insulator at least partially residing in the ferrule opening, where a gold braze hermetically seals the insulator to the ferrule, and where the insulator has a thickness extending between an insulator first side and an insulator second side, and further where at least one via hole extends through the thickness of the insulator, the at least one via hole being provided with a via hole metallization to form at least one metallized via hole, and (c) a conductive fill residing at least partially within the at least one metallized via hole, where the conductive fill hermetically seals and forms a conductive pathway between the insulator first side and the insulator second side to form an electrically conductive hermetic via.

In illustrative embodiments, the conductive fill is a substantially pure gold body. In some embodiments, an adhesion layer contacts an internal surface of the at least one via hole, and a wetting layer resides at least partially on the adhesion layer to form the via hole metallization of the at least one metallized via hole, where, in suitable embodiments, the wetting layer contacts the conductive fill to form the electrically conductive hermetic via. In this respect, the via hole metallization includes one or more materials selected from titanium, iridium, niobium, tantalum, ruthenium, zirconium, palladium, molybdenum, silver, platinum, copper, and carbon, and mixtures thereof.

In suitable embodiments, the insulator is composed of one or more layers of a material at least partially composed of zirconium oxide, sapphire, zirconia toughened alumina (ZTA), and yttria-stabilized-zirconia (YSZ), where the yttria-stabilized-zirconia (YSZ) is a 3 mol % yttria-stabilized-zirconia (3YSZ). The thickness of the insulator, in certain embodiment, is about 20-40 μm. In illustrative embodiments, the feedthrough assembly has a leak rate of no greater than $1 \times 10^{-7}$ std cc He/sec. The feedthrough assembly, moreover, further entails at least one metal cover pad conductively connected to the electrically conductive hermetic via, where the at least one metal cover pad is disposed on either or both of the insulator first side and the insulator second side, in some embodiments.

In illustrative embodiments, a counterbore resides at least partially within the at least one metallized via hole on either or both of the insulator first side and the insulator second side. In some embodiments, the via hole metallization at least partially resides on an internal surface of the at least one via hole, while in certain embodiments, the via hole metallization extends from the internal surface of the at least one via hole to at least a portion of either or both of the insulator first side and the insulator second side, where the conductive fill binds to and substantially covers the via hole metallization. A thick film metallization resides at least partially on either or both of the insulator first side or the insulator second side in suitable embodiments.

The via hole metallization, in suitable embodiments, at least partially resides on an internal surface of the at least one via hole, where the via hole metallization extends from the internal surface of the at least one via hole to at least a portion of either or both of the insulator first side and the insulator second side to form an extended via hole metallization. In some embodiments, the conductive fill substantially covers the extended via hole metallization either alone or in combination with a metal cover pad. In illustrative embodiments, the at least one via hole has a first diameter and the extended via hole metallization has a second diameter, and wherein second diameter is about 2 to 5 times greater than the first diameter.

In one aspect, a flexible substrate assembly is provided, where such an assembly entails: (i) an insulator having a thickness extending between an insulator first side and an insulator second side, (ii) at least one via hole extending through the thickness of the insulator, where the at least one via hole is provided with a via hole metallization residing at least partially on an internal surface of the at least one via hole to form at least one metallized via hole, and (iii) a conductive fill residing at least partially within the at least one metallized via hole, where the conductive fill hermetically seals and forms a conductive pathway between the insulator first side and the insulator second side to form an electrically conductive hermetic via.

In illustrative embodiments, the via hole metallization extends from the internal surface of the at least one via hole to at least a portion of either or both of the insulator first side and the insulator second side, where the conductive fill binds to and substantially covers the via hole metallization. A thick film metallization is provided in some embodiments, where the thick film metallization resides at least partially on either or both of the insulator first side and the insulator second side. In some embodiments, the conductive fill is a substantially pure gold body. The via hole metallization include, in certain embodiment, one or more materials selected from titanium, iridium, niobium, tantalum, ruthenium, zirconium, palladium, molybdenum, silver, platinum, copper, and carbon, and mixtures thereof.

In illustrative embodiments, the insulator includes one or more layers of a material at least partially composed of zirconium oxide, sapphire, zirconia toughened alumina (ZTA), and yttria-stabilized-zirconia (YSZ), where the YSZ is a 3 mol % yttria-stabilized-zirconia (3YSZ). Certain embodiments include an insulator having a thickness of the insulator is about 20-40 μm. In illustrative embodiments, the flexible substrate assembly has a leak rate of no greater than $1 \times 10^{-7}$ std cc He/sec. At least one metal cover pad conductively connected to the electrically conductive hermetic via is provided, in some embodiments, where the at least one metal cover pad is disposed on either or both of the insulator first side and the insulator second side.

In one aspect, the present disclosure concerns a feedthrough assembly that includes: (a) a ferrule having an electrically conductive material, the ferrule entailing a ferrule opening, where the ferrule is configured to be attachable to an opening in a housing of a medical device, (b) an insulator at least partially residing in the ferrule opening, where a gold braze hermetically seals the insulator to the ferrule, the insulator entailing: (i) a thickness extending between an insulator first side and an insulator second side, (ii) a thick film metallization residing at least partially on either or both of the insulator first side and the insulator second side to form a metallized insulator, and (iii) at least one via hole extending through the thickness of the metallized insulator, (c) a fritted conductive fill residing at least partially within the at least one via hole, where the fritted conductive fill hermetically seals and forms a conductive pathway between the insulator first side and the insulator second side to form an electrically conductive hermetic via.

In suitable embodiments, the fritted conductive fill is selected from a glass-fritted metal body, a ceramic-fritted metal body, a glass and ceramic fritted metal body, and combinations thereof, where the fritted metal body is a metal selected from titanium, tantalum, niobium, gold, palladium, silver, molybdenum, and platinum, and combinations thereof. In some embodiments, the insulator comprises one or more layers of a material at least partially composed of zirconium oxide, sapphire, zirconia toughened alumina (ZTA), and 3 mol % yttria-stabilized-zirconia (3YSZ).

In some embodiments, the thickness of the metallized insulator is about 20-40 μm. The feedthrough assembly possesses a leak rate of no greater than $1 \times 10^{-7}$ std cc He/sec. At least one metal cover pad conductively connected to the electrically conductive hermetic via is provided in certain embodiments, where the at least one metal cover pad is disposed on either or both of the insulator first side and the insulator second side. An adhesion layer at least partially contacts either or both of the insulator first side and the insulator second side, in some embodiments, and a wetting layer residing at least partially on the adhesion layer to form the thick film metallization.

In one aspect, the present disclosure is directed to a method of manufacturing a feedthrough assembly, the method having the steps of: (a) providing a ferrule composed of an electrically conductive material, the ferrule including a ferrule opening, where the ferrule is configured to be attachable to an opening in a housing of a medical device, (b) providing an insulator having a thickness extending between an insulator first side and an insulator second side, where the insulator is configured to at least partially reside in the ferrule opening, (c) introducing at least one via hole to the insulator, where the at least one via hole extends through the thickness of the insulator, (d) providing at least one conductive filling to at least partially infiltrate the at least one via hole, and (e) subjecting the feedthrough assembly to at least one heating step to hermetically seal and form a conductive pathway between the insulator first side and the insulator second side, where the at least one heating step separately, sequentially, or simultaneously, forms a hermetic connection between the ferrule and the insulator.

In illustrative embodiments, the at least one conductive filling includes one or more of a via hole metallization, a fritted metal paste, a substantially pure metal paste, and a substantially pure metal body, where the fritted metal paste, the substantially pure metal paste, and the substantially pure metal body are a metal selected from titanium, tantalum, niobium, gold, palladium, silver, molybdenum, and platinum, and combinations thereof, in some embodiments. In illustrative embodiments, the methods further include the step of providing a thick film metallization to the insulator after step (b) and prior to step (c) to form a metallized insulator, where the thick film metallization at least partially resides on either or both of the insulator first side and the insulator second side.

A via hole metallization is provided in some embodiments, such that the metallization at least partially resides within the at least one via hole after step (c) and prior to step (d) to form at least one metallized via hole. The via hole metallization is composed of one or more metals selected from the group consisting of niobium, molybdenum, palladium, and platinum, and mixtures thereof, in illustrative embodiments. The methods further define that step (b) includes sintering one or more layers of a material selected from 3 mol % yttria-stabilized-zirconia (3YSZ), zirconium oxide, sapphire, and zirconia toughened alumina (ZTA), and mixtures thereof. The insulator is provided in a green state in suitable embodiments.

In illustrative embodiments, the introducing of step (c) is a laser drilling, punching, machining, or waterjet cutting, while is some embodiments the methods further include an insulator sintering after the step (c) introducing. In certain embodiments step (b) entails performing a tape casting process to form one or more layers of a material selected from 3 mol % yttria-stabilized-zirconia (3YSZ), zirconium oxide, sapphire, and zirconia toughened alumina (ZTA), including combinations and mixtures thereof.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE FIGURES

FIGS. 1A-1B show cross-sectional views of an illustrative representation of a flexible hermetic membrane possessing the electrically conductive hermetic vias of the preset invention. FIG. 1A is an elongated view, showing multiple electrically conductive hermetic vias provided with a via hole metallization, as illustrated. FIG. 1B is an enlarged view, showing an electrically conductive hermetic via possessing a via hole metallization with respect to the present invention.

FIGS. 2A-2C show cross-sectional views of an illustrative representation of flexible hermetic membrane possessing the electrically conductive vias of the preset invention. FIG. 2A is an elongated view, showing multiple electrically conductive hermetic vias possessing a via hole metallization extending from an internal via hole surface to a surface external to the via hole as illustrated. FIG. 2B is an enlarged view, showing an electrically conductive hermetic via possessing the via hole metallization and extensions therefrom, of the present invention. FIG. 2C is an enlarged view, showing dimension ratios with respect to an electrically conductive hermetic via and the via hole metallization with extensions therefrom, of the present invention. FIG. 2C further illustrates an embodiment showing the flexible membrane hermetically bonded to a ferrule through an adhesion layer and wetting layer of a metallization.

FIG. 3 is an isometric view of an illustrative representation of a flexible hermetic membrane with multiple electrically conductive vias of the preset invention.

DETAILED DESCRIPTION

Figure 2C:
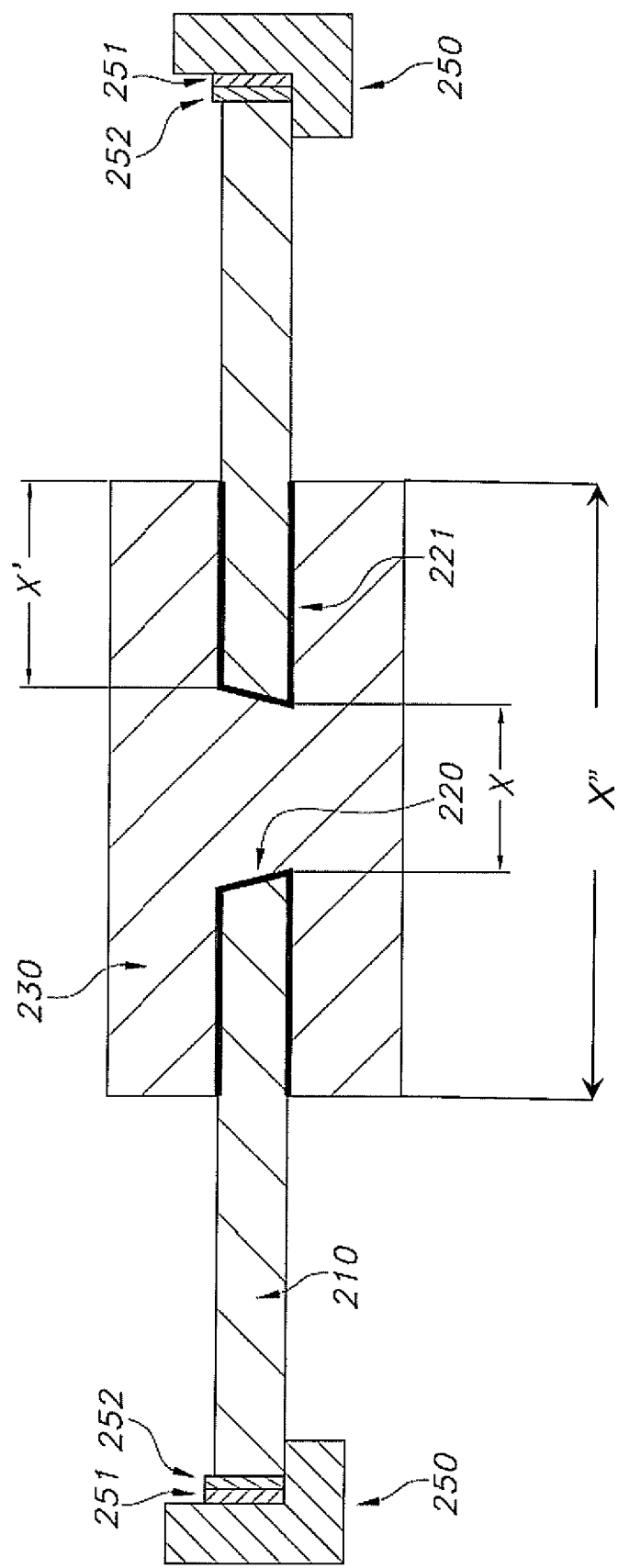

In the following detailed description, reference is made to the accompanying drawings, which form a part thereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

As used herein, unless otherwise stated, the singular forms "a," "an," and "the" include plural reference. Thus, for example, a reference to "an insulator" can include a plurality of insulators.

As used herein, the term "about" will be understood by persons of ordinary skill in the art and will vary to some extent depending upon the context in which it is used. If there are uses of the term which are not clear to persons of ordinary skill in the art, given the context in which it is used, the term "about" in reference to quantitative values will mean up to plus or minus 10% of the enumerated value.

As used herein the term "alloying" refers to a substance that is a homogeneous hybrid of two or more elements, at least one of which is a metal, and where the resulting material possesses at least some metallic characteristic properties. Along the same lines, the term "compounding," as used herein, refers to a chemical compound that is a substance consisting of two or more elements chemically-bonded together in a fixed proportion by mass. "Diffusion solution formation," moreover, as used herein, refers is the net movement of particles from an area of high concentration to an area of low concentration. A solid solution is a solid-state solution of one or more solutes in a solvent. Such a mixture is considered a solution rather than a compound when the crystal structure of the solvent remains unchanged by addition of the solutes, and when the mixture remains in a single homogeneous phase.

The terms "assessing" and "evaluating" are used interchangeably to refer to any form of measurement, and includes determining if an element is present or not. The terms "determining," "measuring," "assessing," and "assaying" are used interchangeably and include both quantitative and qualitative determinations. Assessing may be relative or absolute. "Assessing the presence of" includes determining the amount of something present, as well as determining whether it is present or absent.

As used herein, the terms "binder" or "binders" refers to polymers or materials that facilitate adhesion, connection, coupling, binding, attachment, affixation, or joining of two or more of the materials disclosed herein, e.g., substrate, insulator, adhesion and wetting layers, metallization layers, conductive fills, metallic pastes, gold bodies, etc. In some embodiments, the binders include, but are not limited to, alkyds, acrylics, vinyl-acrylics, polyurethanes, polyesters, melamine, epoxies, silanes, and siloxanes, and combinations thereof.

As used herein, the term "biocompatible," refers to, and includes the terms, "biocompatible material," "biocompatible materials," "biocompatible composition," or "biocompatible polymers," which denotes a synthetic or natural material that is, for example, non-toxic to biological systems and/or congruent with biological processes. In this respect, biocompatibility of polymeric materials specify minimal, negligible, or no risk of immunorejection, injury, damage and/or toxicity to living cells, tissues, organs, and/or biological systems. In illustrative embodiments, the biocompatible materials constitute, at least partially, one or more components of the feedthrough assemblies and flexible substrate assemblies disclosed herein.

As used herein, the term "braze" or "brazing" refers generally to the forming, fixing, or joining by soldering with an metal or metal alloy at high temperature. More specifically, brazing refers to a metal-joining process in which two or more metal components are joined together by melting and flowing a filler metal into a joint, the filler metal typically possessing a lower melting point than the adjoining metal.

As used herein, the term "conductive pathway" refers generally to an electrical connection from an external to internal component of a medical device, device, feedthrough, feedthrough assembly, and the like. The term may also refer to the "conductive pathway" of one or more electrically conductive vias, which may be infiltrated with a conductive paste, fill or material, extending from an insulator first side to an insulator second side. Likewise, to the extent that a lead, pins, conductor, leadwire, and the like, are present within one or more of conductive interconnects or vias, the term "conductive pathway" can also refer to the implementation of such components within a device or conduit.

Along these lines, and as described herein, composite, fritted, and/or metal filled, e.g., containing a gold body or conductive fill, the conductive vias, e.g., that are filled vias passing through an insulator in a nonconductive relationship with a ferrule, in some embodiments, function in an electrical manner in the same way as a leadwire, lead, or pin would with respect to the electrical connection. Such paste filled or gold body containing vias may also incorporate metallizations layers in certain embodiments.

As used herein, the terms "compartment" or "compartments" refer to devices or chambers that support an implantable medical device of the present invention, such a compartment may be a housing, for example, which functions as an outer casing of such devices. A compartment may have various environmental conditions, such as, but not limited to, electrolytic species, metal and/or gas content, e.g., air, oxygen (or lack of oxygen), nitrogen (or lack of nitrogen), carbon dioxide, electrode materials, conductors, voltage biases, temperatures, insulative properties, as well as hermetic barriers. Compartments can be of any size, shape, or material, and of any configuration that will physically maintain the various components of an implantable medical device of the present invention, but, in many instances, such compartments are hermetic and very small or miniaturized, e.g., possessing one or more components having dimensions in the micron $10^{-6}$ range.

As used herein, the term "composition" refers to a product, material, device or component with specified or particular materials, polymers, compounds, etc., in the specified amounts, as well as any products or the generation of such products which result, directly or indirectly, from combination of the specified items in the specified amounts.

The terms "coupled," "connected," and the like, as used herein mean the joining of two members directly or indirectly to one another. Such joining may be stationary, e.g., permanent, or moveable, e.g., removable or releasable. Such joining may be achieved with the two members or the two members and any additional intermediate members being integrally formed as a single unitary body with one another or with the two members or the two members and any additional intermediate members being attached to one another. Such terms, in some embodiments, may refer to a physical and/or conductive, i.e., electrical, joining or communication between two or more components or members of the present invention.

As used herein, the terms "disengage" or "disengaged configuration", both refer to act or state of no longer being securely associated or connected. For example, two components are disengaged with each other they are not in physical contact with each other. However, such components can be in contact while concomitantly occupying a disengaged state. In this circumstance, the components would not be securely engaged by such means as, for example, a locking mechanism. If such components are "reversibly disengaged" then the components are capable of engaging at a different time. The foregoing holds true for an engagement or disengagement with respect to an electrical or conductive connection.

As used herein, the terms "engage", "reversible engage", "reversibly engaged", and "engaged configuration" all refer to the act or state of being associated or connected in a secure manner for the purpose of joining two or more components for a period of time. For example, two components are engaged with each other when they are in contact and securely connected or associated for a period of time. To be in the engaged state, the components are in contact while concomitantly occupying an engaged state, such as, for example, a locked state. If such components are "reversibly engaged" then the components can be engaged and disengaged with respect to the features enabling such association and disassociation, respectively. The foregoing holds true for an engagement or disengagement with respect to an electrical or conductive connection.

As used herein, the term "encapsulation" or "encapsulating" refers to the retention of substance within a compartment, delineated by a physical barrier. For example, the encapsulated components described herein refer to components which are retained within, and surrounded by a physical barrier, such as a pocket or seal, which may or may not possess hermeticity. For a barrier, seal, connection, compartment, and the like, to be hermetic, as defined herein, such an enclosed space must be airtight, and possess a leak rate of no greater than $1 \times 10^{-7}$ std cc He/sec.

As used herein, an "electrochemical cell" or "cell," refers to, for example, but is not limited to, a primary or secondary battery that has sufficient energy density and discharge capacity in order to be a suitable power source for an implantable medical device. Contemplated medical devices include implantable cardiac pacemakers, defibrillators, neurostimulators, drug pumps, ventricular assist devices, and the like.

It should be noted that the term "exemplary" as used herein to describe various embodiments is intended to indicate that such embodiments are possible examples, representations, and/or illustrations of possible embodiments, i.e., where such terms are not intended to connote that such embodiments are necessarily extraordinary or superlative examples with respect to the referred to embodiments of the present invention.

As used herein, an "implantable medical device," "medical device," or, in some instances, as context dictates, a "device," includes component systems and apparatuses, entailing, for example, but not limited to, electronic circuits disposed within the human body that have a primary or secondary battery, or have an alternative energy source, such as energy induced by motion, thermal or chemical effects or through external induction. Unless stated otherwise, as referred to herein, the implantable medical devices possess constituent components such as, for example, but not limited to, a flexible insulator substrate, at least one via hole, metallized or otherwise, one or more conductive throughholes, vias, via holes, interconnections, interconnect, channels, internal, external, via hole and/or thin or thick film metallization layers, a conductive fill, component, body, paste, etc., and, in some embodiments, a conductive ferrule possessing an opening.

As used herein, the terms "insulator," "insulative body," "insulator body," "substrate," "membrane," "ceramic substrate," and the like, refer to the compositions, layer or layers of material that are employed as materials to insulate a conductive pathway from a surrounding material, such as, for example, a ferrule.

As used herein, the term "paste" or "conductive fill" generally refers to epoxies, inks, gels, slurries, paints, sheets, cermets, pastes, fritted metal composites, solidified and/or stable metallic bodies, such as, for example, a gold body, and other such metal and/or metal-ceramic sinterable material combinations, that can be flowable, injectable, pressed, pulled, pushed or otherwise movable into an orifice or via, depending on the temperature and state of such material. Post-sintering, the solvents and binders included in such materials are typically baked out, and, after sintering, the paste, for example, becomes a densified solid with a monolithic structure, in illustrative embodiments.

As used herein, "prevention" or "preventing" of a result or condition refers to a method or process that, in a statistical sample, reduces the occurrence of, for example, loss of hermeticity, in a sample feedthrough assembly relative to a control assembly.

As used herein, the term "sintering" refers to the consolidation of the substrate, insulator, or ceramic material during heating or firing. Consolidation, in this regard, connotes that, within the ceramic material, particles have joined together into a bonded aggregate possessing a cohesive stability. "Sintering" may be used with respect to defining that the substrate, insulator, or ceramic material has condensed. Likewise, "sintering," as referred to herein, also denotes a method of forming solitary structures from a powder, by heating the material below its melting point until its particles adhere to each other. The same term is also commonly and traditionally used in referring to the manufacture of ceramic objects, and also finds similar denotation in the arena of powder metallurgy.

As used herein, the terms "strain-at-break," "strain break," "ultimate elongation," or "elongation to break" refer to the strain on a substrate, insulator body, materials in the green state prior to sintering, materials after being subjected to sintering, pellets, layers, tapes, and other forms of the flexible substrate assemblies of the present disclosure, when it fractures or breaks, which is expressed as a percentage.

As used herein, the terms "substantial" or "substantially" within the context of a "substantially enveloped" surface or region or a "substantially aligned" configuration, refer to, e.g., total or complete envelopment, encapsulation or alignment, and the like, but also includes lesser than complete or total envelopment, encapsulation or alignment, and the like, insofar as the intended purpose for performing the act can be carried out to the same extent as if the, e.g., envelopment, encapsulation or alignment, were total or complete.

As used herein, the term "surgically operative" or "operative," when used within the context of a device or medical device possessing a feedthrough assembly of the present invention, refers to such devices that, in the absence of any material or critical defects unrelated to the integral indicators of the present invention, are capable of being employed by a clinician for a medical procedure. In contrast, the terms "surgically inoperative" or "inoperative," when used within the context of a device or medical device possessing a feedthrough assembly of the present invention, refers to such devices that are at least in part not suitable for implantation into a patient.

As used herein, the terms "tensile modulus," "elastic modulus," or "Young's modulus," refer to the degree of resistance, typically measured in gigapascals (GPa), a material possesses with respect to elastic deformation.

As used herein, the term "tensile strength" refers to the ability of a material to withstand longitudinal stress, expressed as the greatest stress that the material can endure without breaking or fracture. Typically, tensile strength is measured in megapascals (MPa) or pounds per square inch (PSI), where a MPa is equivalent to 145 PSI.

As used herein, the terms "via," "via hole," "interconnect," "passage," "passageway," "throughhole," "channel," "pathway," "conductive pathway," "conductive conduit," and the like, are all used interchangeably with respect to a space formed through a substrate or insulator residing within a feedthrough assembly. In illustrative embodiments, such a via is metallized, infiltrated with a conductive fill, and, accordingly, hermetic and electrically conductive.

As used herein, the term "wettability" or "wetting" refers to the ability of a substance to maintain surface contact with a different substance or surface. Surface contact results from intermolecular interactions between a substance and the contacted surface. Wetting, and the surface forces that control wetting, are also responsible for other related effects, including capillary action or capillary effects. In this regard, the wettability, or degree of wetting, can be calculated in terms of the force balance between the adhesive and cohesive forces. Wettability can be altered by, for example, adding different combinations and concentrations of materials to, for example, components of a feedthrough assembly.

Introduction

The present technology relates to electrical feedthrough assemblies and methods of fabricating such feedthroughs, including their constituent insulator substrate assemblies, which contain electrically conductive hermetic vias in illustrative embodiments. The feedthrough assemblies disclosed herein typically pertain to implantable indications requiring very small or miniaturized medical device components, including ultra-thin insulator substrates, in some embodiments.

Electrical feedthroughs function by providing a conductive pathway extending from the interior of a hermetically sealed housing to a locus external to the housing. Implantable medical devices, such as, for example, implantable pulse generators (IPGs) for cardiac pacemakers, implantable cardioverter/defibrillators (ICDs), nerve, brain, organ, and muscle stimulators, and implantable monitors, employ such electrical feedthroughs through their housing to establish conductive communication with various electrical components, such as, for example, leads, electrodes, and sensors, which reside external to the housing, in suitable embodiments.

Feedthroughs, to this end, typically include a ferrule adapted to be positioned within a housing opening, one or more conductive components, and a non-conductive hermetic insulator composed of, e.g., a glass, metal-composite, or ceramic seal, which supports and electrically isolates each such conductive component from the ferrule and any other conductors passing through it, if applicable. The device housing, moreover, is typically composed of a biocompatible metal, e.g., titanium, although non-conductive ceramics materials have been proposed for forming the same. See, e.g., PCT International Publication No. WO 2011/025667, the entire contents of which are hereby incorporated by reference in its entirety. In many instances, the ferrule is composed of a metal that can be welded or otherwise hermetically adhered to the housing.

For certain indications, it may be necessary to chronically implant such medical devices to enable continuous bioelectronic interactions between the implanted device and the local region of the patient being monitored. However, to the extent that some or any of the component materials constituting such devices lack biocompatibility, a hermetic seal may be required to sequester those components in the device housing, i.e., to prevent the escape of potentially harmful materials into the vasculature of a patient. And, at least with respect to patient safety in this regard, the hermetic integrity of the device is paramount.

Nevertheless, the hermeticity borne out of the components and processes described herein, contemporaneously afford protection to the electrical components of the device, along the same lines, i.e., from the potential ingress of moisture and the corrosive infiltrates of a patient body fluids that could otherwise infiltrate to the circuitry of the device. It is accordingly desirable that such device feedthrough assemblies comport with stringent standards pertaining to implantable device hermeticity, while also possessing pliability with respect to the insulator substrate to ensure fracture resilience, i.e., to maintain hermeticity, yet with sufficient rigidity to support one or more electrically conductive via holes.

To this end, various insulator structures and conductor materials may be employed with respect to single and multiple conductor feedthroughs. In concert with functioning as a non-conductive insulator, these substrate structures further establish feedthrough hermeticity typically subsequent to sintering in the presence of additional metallic layers or materials to prevent ingress of body fluids through the feedthrough and into the IMD housing. Traditionally, however, large single pin feedthrough conductors were employed, and, accordingly, supported in bulky, rigid, ceramic-glass, insulator substrates that require significant component volume, which also may not survive device fabrication processes or properly function within the locally implanted region of a patient.

In response to changing needs, however, smaller case sizes are being used, while the number of external leads, electrodes, and/or sensors that are coupled with the circuitry of the IMD have increased. Consequently, use of relatively large single pin feedthroughs is no longer feasible for many applications, where miniaturized assemblies and/or multiple conductor feedthroughs are desired for certain applications. And, while reducing the size of feedthrough pins would facilitate, to a certain extent, device and feedthrough miniaturization, the comprehensive elimination of such components, while maintaining electrical conductivity and hermeticity, imparts a paradigmatic shift with respect to the design, manufacture and application of the same.

Co-fired ceramic layer substrates possessing conductive pathways in the absence of terminal pins, e.g., formed of traces or vias, nonetheless have been disclosed. See, e.g., U.S. Pat. Nos. 4,420,652; 5,434,358; 5,782,891; 5,620,476; 5,683,435; 5,750,926 and 5,973,906, all of which are hereby incorporated by reference in their entirety. However, in conjunction with the above-cited disclosures, traditional feedthrough insulator substrates composed of ceramic, glass, or metal-ceramic, typically require additional polymer protection to remain hermetic under implanted conditions due to the instabilities associated with such traditional ceramic-to-metal interfaces in the presence of corrosive body fluids. In addition to loss of hermeticity, in this respect, micro-fractures in the insulator substrate may precipitate from the stresses attendant to processes, such as, for example, sintering, brazing and/or welding.

The prior art is nevertheless absent conductive pathways pertaining to single or multiple conductive hermetic vias supported in a miniaturized, i.e., very thin, metallized flexible substrate that is fracture resilient, durable, biocompatible and configured for most any implantable indication, as disclosed herein. Such feedthrough assemblies of the present disclosure have an internally disposed portion configured for electrical connection with the internal circuitry and an externally disposed portion configured for ultimate conductive communication with various downstream components. In accord with the elimination of conductor pins, leads, leadwires, and the like, in some embodiments, the present technology comports with miniaturized device applications at least insofar as the insulator substrates disclosed herein, in some embodiments, are composed of flexible, ultra-thin, materials, such as, for example, 3 mol % yttria-stabilized-zirconia (3YSZ), in illustrative embodiments.

Accordingly, the present disclosure is directed toward hermetic feedthrough assemblies supported by thin flexible substrate insulators, possessing electrically conductive hermetic vias, that function as mechanical and electrical interfaces between the sensitive internal circuitry of an implantable medical device and the corrosive external body tissue environment, while maintaining an essential conductive pathway.

Technology Design Overview

The hermetic feedthrough assemblies of the present disclosure entail, in illustrative embodiments, a ferrule composed of an electrically conductive and biocompatible material, such as, for example, titanium, where the ferrule has an opening, which is essentially the feedthrough opening or reservoir. The ferrule is also configured to be attachable to an opening in a housing of an implantable medical device in illustrative embodiments. Such medical devices include, but are not limited to, pacemakers, implantable cardioverter-defibrillators, sensors, cardiac contractility modulators, cardioverters, drug administering devices, diagnostic recorders, cochlear implants, and other similar devices.

The feedthrough assemblies further entail an insulator at least partially residing in the ferrule opening, where a gold braze hermetically seals the insulator to the ferrule, in some embodiments. Additional or alternative mechanisms for hermetically sealing an insulator and ferrule are generally knowing the art, and include, but are not limited to, for example, glass/ceramic sealing, brazing, compression fitting, co-firing or sintering in the presence of bonding materials or agents, binders, solvents, etc., sintering and densification, injection molding, and over-molding. See, e.g., U.S. Patent Pub. No. 2011/0048770, which is hereby incorporated by reference in its entirety.

Mating surfaces on an insulator substrate may be metallized with a refractory or precious material, such as, e.g., but not limited to niobium, titanium, gold, molybdenum, tungsten, palladium, platinum, and combinations thereof, in some embodiments. Metallization, in this regard, may be applied by standard physical or chemical deposition methods that are commonly used in the industry. Gold and titanium are employed, in some embodiments, due to the associated biocompatible properties and relative melting temperatures. Likewise, the perimeter or surrounding side walls of an insulator are metallized or coated, e.g., by a variety of methods, such as, but not limited to, physical vapor deposition, sputtering, electron-beam evaporation, plating, thin and/or thick film application processes, chemical vapor deposition, etc., with a metal, such as niobium, titanium, molybdenum, or other biocompatible materials, to facilitate joining between metal or fritted composite layers and/or between the insulator and the ferrule, in illustrative embodiments.

A conductive ferrule supports the insulator substrate, in some embodiments, which may possess a perimeter metallization, composed of an adhesion layer and a wetting layer, in certain embodiments. The insulator, moreover, includes one or more conductive channels or vias that extend through the thickness of the insulator. The internal surface of the via holes, in illustrative embodiments, possesses a via hole metallization, which also includes an adhesion layer and a wetting layer, to improve the coefficient of thermal expansion (CTE) matching, if required, while facilitating the bonding interaction, with a conductive fill, such as, for example, a metal paste or body, e.g., a gold paste or gold body. In addition to establishing the conductive pathway of the feedthrough assembly, the conductive fill ultimately imparts hermeticity to the flexible substrate after being subjected to high temperatures, e.g., sintering, in some embodiments.

In some embodiments, the insulator substrate is at least partially composed of, for example, sapphire, yttria-stabilized-zirconia (YSZ) or zirconia-toughed-alumina (ZTA), in suitable embodiments, while additional or alternative materials for such insulators are further disclosed herein. In some embodiments, the YSZ is a 3 mol % YSZ or "3YSZ." In addition to pliability, these ultra-thin substrates, e.g., ranging from about 1-50 μm, or from about 20-40 μm, in some embodiments, are sufficiently stable to support a plurality of electrically conductive hermetic vias, which further underscores their utility with respect to the present embodiments. The flexibility of the insulator body, in combination with the conductivity and hermeticity of the conductive fill, e.g., gold body, impart a significant advance over traditional substrate materials, which are measurably more fragile in comparison, as further detailed herein.

Hermetic feedthrough assemblies utilizing traditional dielectric materials, e.g., glass-ceramic composites, in this respect, fail insofar as these brittle insulator materials are prone to fracturing subsequent to sintering. Brittle failure typically occurs when a ceramic structure, substrate, insulator body, etc., reaches an intolerable stress with respect to its elastic deformation, strain-at-break, tensile modulus, and/or elastic modulus, at which point the structure catastrophically fails. Most brittle failures occur by crack propagation in a tensile stress field, however. Microcracking caused by sufficiently high tensile stress concentrations may also result in a catastrophic failure, including loss of hermeticity.

Loss of hermeticity may also result from other factors, such as those relating to design defects, e.g., ridged insulator body corners and/or mating materials that possess significantly disparate coefficients of thermal expansion (CTE), which consequently generate tensile stresses that result in loss of hermeticity with respect to the feedthrough or via structure. Feedthrough assembly miniaturization, including circumstances where ultra-thin substrates are employed, potentially increases the possibility of precipitating a breach in hermeticity, e.g., at least due to the increased difficulty associated with forming and filling small diameter via holes within a micron-sized substrate. Using flexible insulators as provided herein, e.g., 3 mol % YSZ and/or sapphire, however, obviate many concerns with respect to substrate fragility.

Other variables affecting the type and magnitude of stress that feedthrough assembly designs will encounter, include, but are not limited to, indispositions with respect to the design specification, improper or unavailability of suitable materials selection, feedthrough asymmetry, and intermolecular incompatibility of the feedthrough bonding surfaces. As such, and in concert with topological considerations relating to the pitch, density, and diameter of the conductive pathways, e.g., the electrically conductive hermetic vias, the physical dimensions and overall functionality of the feedthrough assemblies typify the myriad combination of design and manufacture considerations that portend a loss of hermeticity, if not carefully addressed.

Likewise, the fabrication processing parameters, particularly at via hole formation and metallization, binder burnout, sintering, and incubation, are directly related to the relative fragility or flexibility of an overall feedthrough assembly structure. One of the most critical features of a feedthrough design concerns the metal-ceramic interface that functions to establish the hermetic seal within the feedthrough. Some embodiments of the present invention accordingly provide for a hermetic feedthrough that entails a ceramic-based insulator substrate within which a gold, or other similar metal forming, conductive pathway resides. More specifically with respect to electrically conductive filled vias, the present invention provides a hermetic feedthrough in which the hermetic seal is created through the intimate bonding of the ceramic substrate with a conductive fill through one or more metallization layers, in illustrative embodiments, as further detailed herein.

In short, the device assemblies and methods provided herein pertain to flexible substrate feedthrough assemblies composed of, in part, an insulator body possessing one or more metallized via holes, in some embodiments, that ultimately functions as the feedthrough conductive pathway, i.e., following infiltration of the conductive fill, which, in some embodiments, is a metallic paste, metallic fill, and/or a substantially pure metallic body, such as, for example, a substantially pure gold body. In illustrative embodiments, the feedthrough assemblies and flexible substrates of the present invention are both biocompatible and electrochemically stable, i.e., and accordingly suitable for implantation in a patient's body.

Electrically Conductive Hermetic Vias

Further to the foregoing overview, and with reference to accompanying FIGS. 1-3, various aspects of the present disclosure, as detailed herein, relate to hermetic feedthrough assemblies that are configured for functional operation in corrosive environments, e.g., in medical devices intended for implantation into a patient's body. As such, the feedthrough assemblies of the present invention entail a ferrule 250 having a ferrule opening, where the ferrule is composed of, for example, a conductive material selected from, but not limited to, titanium, substantially pure titanium, nano-titanium, titanium-6Al-4V, titanium-vanadium, and nickel-titanium, titanium-niobium, and mixtures thereof. In certain embodiments, the ferrule is further composed of one or more materials selected from niobium, platinum, molybdenum, zirconium, tantalum, vanadium, tungsten, iridium, rhodium, ruthenium, palladium, silver, stainless steel, nickel super alloy, nickel-cobalt-chromium-molybdenum alloy, alloys of these metals, and combinations thereof.

The ferrule further includes a ferrule opening, where the ferrule is configured to be attachable to an opening in a housing of a medical device through a ferrule flange. In accord, the insulators of the present disclosure at least partially reside in the ferrule opening, where a hermetic seal between the insulator, which includes a metallized layer 252, as shown in FIG. 2C, and the ferrule is formed of a gold braze 251, in illustrative embodiments. Additional or alternative mechanisms for hermetically sealing an insulator and ferrule are generally known the art, and include, but are not limited to, for example, glass/ceramic sealing, brazing, compression fitting, co-firing or sintering, sintering and densification, injection molding, and over-molding. See, e.g., U.S. Patent Pub. No. 2011/0048770, which is hereby incorporated by reference in its entirety.

The insulators of the present disclosure, as shown in FIGS. 1-3, entail at least one component of the flexible substrate assemblies 100, 200, 300 provided herein. Such assemblies are composed of an insulator 110, 210, 310, having an insulator first side 111, 211, 311 and an insulator second side 112, 212, 312 where the insulator possesses a thickness 140, 240, 340 extending between the insulator first and second sides. Along these lines, the flexible substrate, insulator, membrane, ceramic material, etc., in certain embodiments, is composed of a sintered, i.e., brown state, or green state ceramic pellet, or one or more layers, sheets, membranes, laminates, etc., of the sintered or green state ceramic material. Such insulators, in some embodiments, may also entail a ceramic tape formed using a tape casting process as further detailed herein.

The flexible substrate assembly insulators disclosed herein are at least partially composed of one or more laminated, sintered, or green state materials selected from yttria-stabilized-zirconia (YSZ), 3 mol % yttria-stabilized-zirconia (3YSZ), zirconium oxide, partially-stabilized-zirconia (PSZ), magnesia-stabilized-zirconia (MSZ), ceria-stabilized-zirconia (CSZ), sapphire, alumina, zirconia, zirconia toughened alumina (ZTA), aluminum nitride, boron nitride, silicon carbide, and glass, and mixtures thereof, in illustrative embodiments. In some embodiments, the insulator body is at least partially composed of a three percent molar yttria-stabilized-zirconia (3YSZ).

With respect to YSZ, electrical and thermal characterizations of this ultra-thin flexible ceramic substrate, i.e., 3 mol % Yttria Stabilized Zirconia (3YSZ), have been explored with respect to various electronic applications. See Zhao et al., "Thermal and Electrical Characterizations of Ultra-Thin Flexible 3YSZ Ceramic for Electronic Packaging Applications." International Symposium on Microelectronics. 2016. 000391-000396. 10.4071/isom-2016-THA13. Thicknesses pertaining to ultra-thin 3YSZ substrates range from about, for example, 20-40 µm, where such properties not only impart a better modulus for higher robustness in manufacturing, but also low thermal resistance for high density applications.

Additional physical properties of 3YSZ, include, for example, a Poisson's ratio of 0.23, a Young's Modulus of 200 GPa, a density of 6.05 g/cm$^2$, a surface roughness of approximately 20.3 Ra, and a coefficient of thermal expansion (CTE) ranging from $8.2\text{-}10.7 \times 10^{-6}/°$ K at room temperature and 1000° C., respectively, which also depend on other factors such as the porosity level and purity of the substrate. When compared to the physical properties of aluminum oxide, which remains the industrial benchmark for ceramic insulators, 3YSZ characteristics are congruent with various thermally conductive metals, such as, e.g., gold, which possesses a CTE of $14 \times 10^{-6}/°$ K, in pure metallic form, to an even closer extent than alumina. In this respect, aluminum oxide or alumina possesses a CTE between $3.6\ 7.3 \times 10^{-6}/°$ K, i.e., depending on factors relating to the percent of oxidized aluminum, temperature and purity. Pure metallic aluminum, however, possesses a CTE of $24 \times 10^{-6}/°$ K.

Nevertheless, certain embodiments of the present disclosure, which do not require the ultra-thin characteristics of 3YSZ, entail a sapphire substrate insulator, which is a single crystal form of corundum, $Al_2O_3$, also known as α-alumina, and single crystal $Al_2O_3$. Sapphire, in short, is aluminum oxide in the purest form with no porosity or grain boundaries, making it theoretically dense. Typically, sapphire substrates range from about 300-800 µm in thickness, which provides a suitable insulative body for applications that require very thin substrate assemblies, but thicker than the YSZ range of about 20-40 µm.

Taken together, the ceramic oxide 3YSZ employed with respect to the present disclosure, in some embodiments, possesses characteristics that are excellent for thin and thick film coatings, while also possessing an ultra-thin thickness in its own regard, e.g., 20-40 µm, which is about 50% the thickness of other available ceramic or glass insulator materials. See, e.g., Schlichting et al., "Thermal Conductivity of Dense and Porous Yttria-Stabilized Zirconia." J. Materials Sci. 36 (2001) 3003-10. In addition to its stable crystal structure over wide range of environments, 3YSZ is resilient to wear and erosion, provides flexibility unmatched by other ceramics at the aforementioned thicknesses, i.e., 3-fold higher flexibility, while its use also permits rapid absorption of environment temperature shifts. See ENrG, Inc., *Material Property Data Sheet for Thin E-Strate Material Properties* (2015). 3YSZ has a bulk thermal conductivity of 2.7 W/mK, which is an order of magnitude greater than glass and 10% that of alumina. See id.

As such, the 3YSZ substrate and interposer provide an assembly framework for interconnections platforms for heterogeneous integration of electrical components, circuits and structures, but also for mechanical, thermal and electrical interfaces between different parts of the systems, devices and methods disclosed herein. See Zhao et al. Its use with respect to higher temperature operations, such as, sintering, makes 3YSZ suitable for metal deposition for thin or thick film applications relating thereto, and for rapid flexible heaters. Critically, however, 3YSZ's CTE compatibility with gold, and other metallization materials, in accord with its ultra-thin profile, establishes a platform for the miniaturization of implantable medical device components, as detailed herein.

Furthermore, 3YSZ is able to withstand the thermomechanical stresses generated by pulsed laser irradiation without exfoliation, where its superior fracture toughness may be attributable to a laser-induced partial transformation of the metastable tetragonal to the stable monoclinic phase. See id. This allows, in contrast to the higher doped fully stabilized YSZ, the growth of particle-free, dense and smooth 3YSZ films by conventional laser deposition processes at moderate fluences, such as, e.g., 1.2-1.5 J/cm$^2$. See Heiroth, S. "Pulsed laser deposition of functional electroceramic thin films for micro solid oxide fuel cell applications," *Doctoral Thesis, Dipl. Chem.*, Heinrich-Heine-Universität Düsseldorf (2010). Such robust, yet flexible, insulative properties accordingly provide a suitable substrate for introducing one or more via holes and/or metalized via holes, while possessing sufficient pliability to withstand processing stresses that emanate from sintering materials that possess poorly matched CTE profiles. With respect to 3YSZ as an insulator, where the conductive fill is a substantially pure gold body, however, stresses attendant to mismatched CTE profiles, are less of a concern compared to traditional insulator materials.

In sum, with respect to YSZ, in conjunction with possessing a CTE that is similar to gold, 3YSZ imparts a robust substrate that remains flexible and durable even at very small micron-range scales. In this respect, inasmuch as 3YSZ and gold possess CTEs that are highly similar, various embodiments of the present invention inure the benefits of 3YSZ at least where the formation of ultra-thin, electrically conductive vias, contemptuously beget a hermetic seal. Not only is 3YSZ a component of the present flexible substrate assemblies disclosed herein, i.e., as a de facto insulator substrate, but coating applications, to this end, may be suitable for various embodiments disclosed herein as well.

Such 3YSZ coatings have been produced by a variety of different deposition techniques, such as, for example, sol-gel chemistry, spin coating, sputtering, pulsed laser deposition, chemical vapor deposition (CVD), and spray pyrolysis, at least with respect to high-k dielectrics in metal-oxide-semiconductor (MOS) technology, buffer layer in superconductor thin film growth, and for miniaturized gas sensors and micro SOFCs. See Rogers et al., J. Phys. Chem. C, 112 (17) (2008), 6749; and Sirinakis et al., J. Phys. Chem. B, 110 (27) (2006), 13508.

Along these lines, due to the low tolerances with respect to via hole positioning, i.e., that is required for thin film processing, laser drilling of the via holes is commonly practiced, and, although laser systems provide precise hole positioning, many problems are associated with this method when using traditional insulator body substrates. Slag and other defects, such as microcracks, are often generated on the substrate within the via hole membrane, i.e., at least when employing glass-ceramic or composite substrate bodies. Such defects can degrade the adhesion and quality of the subsequently applied metallization. Consequently, 3YSZ, and insulator substrates possessing similar properties, such as, for example, sapphire, zirconium oxide, and zirconia toughened alumina (ZTA), are employed with respect to the present disclosure.

Insulator thickness 140, 240, 340 is related to the type of substrate employed and the number of conjoined layers, e.g., through sintering or lamination and compression, insofar as ceramic layers are employed as the starting material, to form the insulative body. Specifically, the formation of the insulator sheets, layers, etc., which, prior to sintering, are in the green state, i.e., as known as a green body, occurs by initially providing one or more layers of substrate material and compressing, fitting, forming, and the like, to achieve the desire body configuration, in some embodiments. The substrate materials are subsequently sintered to generate the insulator body substrate, where, subsequent to the initial sintering, via holes 135, 235, 335 are introduced into the sintered, e.g., brown state, insulator. Alternatively via holes can be introduced into the green body substrate, i.e., prior to the initial sintering, as further detailed herein.

In some embodiments, only a single layer of the ceramic substrate is employed to form the insulator. In other embodiments, a multilayer lamination process is performed to generate the insulator, as noted above, where, in illustrative embodiments, the substrate sheets are stacked on top of each other with or without alignment of the vias, i.e., depending on the order of via introduction with respect to substrate formation. The stacked layers are accordingly sandwiched together and laminated using a heatpress to create a laminated substrate, in certain embodiments.

The insulator body may also be formed as a solid pellet, which is synonymous with a single body of green, pre-sintered, ceramic material, in illustrative embodiments. The ceramic pellet is formed, in certain embodiments, by pressing ceramic paste into a mold or other such forming apparatus, such as, for example, a heat press, compression mold, or through an extrusion process. Regardless of the modality of insulator formation, i.e., either in pellet form or a multilayer stack that is pressed and co-sintered to create a solid body, subsequent to firing, e.g., sintering, the solid pellet becomes indistinguishable from a single- or multi-layer green body.

In either case, firing of the green body, e.g., sintering, or of the laminated substrates, encompasses different aspects of bond formation in the ceramic substrate, such as, for example, evaporation, binder burnout, sintering, etc., all of which depends upon the order of via hole introduction, including associated metallization layers and infiltration of the conductive fill, with respect to the metallized via holes. In suitable embodiments, on the other hand, only a single layer of substrate is required with respect to generating the feedthrough assemblies of the present invention. Nevertheless, such a single layer is sintered in the green state to form the insulator body to which the via holes 135, 235, 335 are introduced, in some embodiments.

The flexible membrane substrates, e.g., insulators of the present invention 110, 210, 310 avoid the aforementioned difficulties at least inasmuch as the stability and flexibility of the, for example, sapphire and/or 3YSZ insulators, can withstand the tensile stresses attendant to laser-applied via hole formation. Likewise, the flexible substrates, insulators, or ceramic materials of the present disclosure, may be formed by using a tape casting process, from a pellet, or from one or more layers of a laminated, sintered, or green state material at least partially composed of zirconium oxide, sapphire, zirconia toughened alumina (ZTA), and yttria-stabilized-zirconia (YSZ), e.g., 3YSZ. In some embodiments, as shown in FIGS. 1-3, the thickness 140, 240, 340 of the insulator 110, 210, 310 extends from an insulator first side 111, 211, 311 to an insulator second side 112, 212, 312.

In particular, feedthrough assemblies are disclosed herein that entail an electrically conductive hermetic via, where the vias 135, 235, 335 are disposed within a flexible substrate assembly having an insulator with a thickness 140, 240, 340 extending between an insulator first side and an insulator second side. In some embodiments, the thickness ranges from about 0.01, 0.1, 1, 0.25, 0.5, 0.75, 1, 3, 5, 7, 9, 10, 15, 20, 30, 50, 100, 500, or 900 µm to from about 0.1, 0.25, 0.5, 0.75, 1, 3, 5, 7, 9, 10, 15, 20, 30, 50, 100, 500, or 900 µm. In some embodiments, the thickness of the insulator ranges from about 5-50 µm or from about 20-40 µm. The thickness 140, 240, 340 of the insulator, in this regard, ranges from about 5-50 µm or from about 20-40 µm, in suitable embodiments.

The present disclosure further entails at least one electrically conductive via hole 135, 235, 335 extending through the thickness 140, 240, 340 of the insulator body 110, 210, 310. In this respect, there are various methods for introducing via holes to a ceramic insulator body, such as, for example, laser drilling, laser ablation, solvent etching, pressing, punching, molding, drilling, machining, laser cutting, laser machining, mechanical drilling, reactive-ion etching, ion-milling, deep reactive ion etching, water-jet cutting, wet etching, waterjet cutting, and the like. Single or multiple vias, channels, throughholes, etc., in this regard, are introduced into the substrate insulator, either in a repeating array or random pattern, using various methods of introducing such orifices, such as those noted above.

The resulting via holes possess various diameter size ranges, such as, for example, a diameter range from about 0.001, 0.01, 0.1, 0.25, 0.5, 0.75, 1, 3, 5, 7, 9, 10, 15, 20, 30, or 50 µm to from about 0.005, 0.01, 0.1, 0.25, 0.5, 0.75, 1, 3, 5, 7, 9, 10, 15, 20, 30, 50 or 100 µm. In certain embodiments, the diameter of the insulator body via holes ranges from about 1-50 µm or from about 2-20 µm. As shown in FIG. 2C, X denotes the diameter of the one or more via holes or metallized via holes.

Along the same lines, certain embodiments of the present invention entail via holes that are formed with a taper, where 125, 225 defines the offset angle with respect to a vertical axis of symmetry, where taper 125, 225 results in a larger via hole diameter on the entry-side of the laser, i.e., when such techniques are employed to introduce the via holes, compared to the exit-side. Tapering feature 125, can best be seen in FIGS. 1B and 2B. Such tapering sterically facilitates infiltration of the conductive fill or conductive filling 130, 230, 330 to the via hole 135, 235, 335 and/or metallized via holes 120, 221, 320, 321 of the present invention.

The via holes, 135, 235, 335 in illustrative embodiments, can also be generated through lithographic techniques. In this respect, the morphology of the via holes is not limiting with respect to the present disclosure, where any shape, e.g., prismatic, triangular, circular, rectangular, etc., is within the scope of the present disclosure. Formation of via holes by lithographic etching, i.e., using lithographically etchable insulating substrates, in some embodiments, serves to reduce the scale of, i.e., miniaturize, an array of feedthroughs when very high channel counts are required, i.e., when an applications requires the formation of dense metallized vias.

And, while substrates containing only a single via hole are within the scope of the present disclosure, laser processing techniques enable high throughput via hole formation that results in increased via hole densities. For example, in some embodiments, the via hole pitch within the insulator body ranges from about 0.01, 0.1, 1, 0.25, 0.5, 0.75, 1, 3, 5, 7, 9, 10, 15, 20, or 30 µm to from about 0.1, 0.25, 0.5, 0.75, 1, 3, 5, 7, 9, 10, 20, 30, or 50 µm. In some embodiments, the pitch ranges from about 1-50 µm, where 200 µm is equivalent to a via hole density of about 600 vias/cm$^2$.

Further concerning thin film application processes, vias are typically formed in substrates, i.e., trace patterns made by vapor deposition or sputtering, by drilling a hole in the substrate and then coating the inside of the hole with one or more thin layers of metal using lithography, vapor deposition, and/or plating processes. This internal via hole metallization 120, 220, 320 resides at least partially within the at least one via hole to form a metallized via hole in some embodiments, as shown in FIGS. 1-3. In suitable embodiments, the via hole metallization extends at least partially to a region outside the via hole 221, 321 e.g., forming an extended via hole metallization, residing at least partially on the insulator first side 111, 211, 311 and/or the insulator second side 112, 212, 312, but nonetheless adjacent to, and extending from, the one or more via holes 135, 235, 335. A thick film metallization, is also formed in some embodiments, on an external membrane surfaces 322, e.g., residing on either or both of the insulator first side 111, 211, 311 or the insulator second side 112, 212, 312.

The internal surface of the via hole 120, 320 and, in some embodiments, the external insulator membrane surface 221, 321 as noted above, is accordingly coated with an electrically conductive material, e.g., a metallization or thin metal film such as for example gold or titanium, when applicable applications require such metallization. The electrically conductive film may be, for example, a single or multi-layer stack, e.g., Ti, Au, Ag, Pt, Pd, Mo, Nb, etc., deposited using, but not limited to physical vapor deposition, chemical vapor deposition, electroplating, sputtering, or atomic layer deposition, etc. In some embodiments, the metallization contains a wetting layer and an adhesion layer.

In this respect, an adhesion layer contacts an internal surface of the at least one via hole, and a wetting layer resides at least partially on the adhesion layer to form the via hole metallization of the at least one metallized via hole. Put simply, the combined adhesion and wetting layers constitute, in some embodiments, the via hole metallization. To this end, the via hole metallization is applied internally to at least a portion of a via hole internal surface 120, 320. Application of the adhesion layer and the subsequent wetting layer, in some embodiments, occurs in a single sputtering operation, while plating operations are also used in various embodiments. In some embodiments, the adhesion layer includes one or more of the materials selected from titanium, iridium, niobium, tantalum, ruthenium, zirconium, palladium, molybdenum, silver, platinum, copper, and carbon, and mixtures thereof.

The adhesion layer material may be selected from a type known to have good adhesion with both the conductive fill and the insulator material, while also being a good electrical conductor. Example materials for the adhesion layer may include, for example, titanium, which possesses excellent adhesion to gold and alumina, or other metals, self-assembled monolayers, or other adhesion promoters. The subsequent wetting layer, moreover, accordingly possesses adhesive properties with respect to the adhesion layer and to the conductive fill, paste, etc. In some embodiments, the wetting layer is composed of Mo, Ti, Nb, Pt or Pd. In illustrative embodiments, the wetting layer one or more of the materials selected from titanium, iridium, niobium, tantalum, ruthenium, zirconium, palladium, molybdenum, silver, platinum, copper, and carbon, and mixtures thereof. An example of a deposition method of the adhesion layer include, for example, physical vapor deposition, e.g., sputter or e-beam, chemical vapor deposition, e.g., atomic layer deposition, plasma enhanced chemical vapor deposition, etc., electrochemical deposition, vapor deposition, etc.

Illustrative embodiments of the present disclosure further entail a conductive fill 130, 230, 330 residing at least partially within the at least one metallized via hole 135, 235, 335. In this respect, the conductive fill 130, 230, 330 hermetically seals and forms a conductive pathway between the insulator first side 111, 211, 311 and the insulator second side 112, 212, 312 to form an electrically conductive hermetic via. In certain instances, the conductive fill may not directly wet to a sintered ceramic body, e.g., YSZ or sapphire, without an intermediate metallization layer, which entails an adhesion and wetting layer, in some embodiments, to which the conductive fill can wet, as noted above.

In this regard, conductive fills 130, 230, 330 of the present disclosure, such as, e.g., a gold paste or gold body, reside at least partially within the metallized via hole such that the conductive fill material forms an electrical pathway and a hermitic seal between the insulator first side and the insulator second side. In this way, the conductive fill, in illustrative embodiments, is selected from a metal paste, ink, epoxy and the like, where the metal can be a noble metal, a refractory metal, a substantially pure metal, or combinations thereof.

In suitable embodiments, methods for filling the at least one via hole with a conductive fill or a paste entail employing a vacuum pull process, a pressure push method, or a squeegee fill technique, or other equivalent process, which is well known in the art. As discussed above, the internal surface of the via hole 120, 320 and, in some embodiments, this via hole metallization extends to the insulator membrane surface 221, 321, as noted above, to metallize that portion with an electrically conductive material, e.g., a metallization or thin metal film. In this regard, the conductive fill 130, 230, 330 in illustrative embodiments, is provided to substantially cover, and bind to, each such metallization surface (see conductive fill 330 with respect to FIG. 3). The gold paste or gold body 130, 230, 330 in some embodiments, binds to, and accordingly covers a portion of the insulator first side and second side, as shown in FIG. 3, regardless of whether a via hole metallization is present, i.e., internal to the via hole and/or extending therefrom onto the insulator first and/or second side.

As noted above, in certain embodiments, the diameter of the insulator body via holes ranges from about 1-50 µm to from about 2-20 µm. FIG. 2C shows the diameter of a metallized via hole as X and the diameter of the extended via hole metallization as X", while X' denotes the vector length between the circumference of the via hole and the extended via hole metallization, which also encompasses the circumference of the conductive fill 230 residing on the extended via hole metallization, i.e., that extends from the via hole internal surface to the insulator first and second sides.

In this respect, in conjunction with the diameter ranges of X that are discussed above, the circumferential relationship between X and X' is defined by a ratio of X:X', which, in some embodiments, is about 1:1, 1:2, 1:3, 1:4, 1:5, 1:6, 1:7, 1:8, 1:9 or 1:10. In illustrative embodiments, the circumferential relationship between X and X" is defined by a ratio of X:X", which, in some embodiments, is about 1:1, 1:2, 1:3, 1:4, 1:5, 1:6, 1:7, 1:8, 1:9 or 1:10. In some embodiments the extended conductive fill 330 is covered by a metal cover pad 331 connected to the conductive fill or gold body on either or both of the insulator first and second sides.

Along the same lines, certain embodiments of the present invention entail via holes that are formed with a taper, where 125, 225 defines the offset angle with respect to a vertical axis of symmetry, where taper 125, 225 results in a larger via hole diameter on the entry-side of the laser, i.e., when such techniques are employed to introduce the via holes, compared to the exit-side. Tapering feature 125, can best be seen in FIGS. 1B and 2B. Such tapering sterically facilitates infiltration of the conductive fill or conductive filling 130, 230, 330 to the via hole 135, 235, 335 and/or metallized via holes 120, 221, 320, 321 of the present invention.

In suitable embodiments, the conductive fill is a metal, e.g., gold, paste, a metal, e.g., gold, braze, a metal, e.g., gold, body, and/or a substantially pure metal, e.g., gold, fill, and combinations thereof. Other metals and compositions contemplated with respect to formulations of the conductive fill, include, but are not limited to, fritted metal composites, glass/ceramic fritted pastes or bodies, Ag, Cu, Pd, Pt, Ti, Mo, Nb, refractory metals, noble metals, precious metals, and the like. The conductive fill may also contain a binder, such as, for example, an acrylic binder, and one or more solvents, dispersants, surfactants, and the like.

Concerning the conductive components within the feedthrough assemblies of the present invention, the conductive fill hermetically seals and forms a conductive pathway between the insulator first side and the insulator second side to form an electrically conductive hermetic via. Various formulations and compositions pertain to the conductive fill with respect to the present disclosure, all of which will be detailed within the various contexts of particular embodiments. Nevertheless, when illustrative embodiments of the present disclosure entail via hole metallizations, one of the preferred conductive fill compositions is a substantially pure gold body.

In this respect, embodiments of the present disclosure entail substantial purity within the range of about 50%, 60%, 70%, 80%, 90%, 95% or 99% in some embodiments. In some embodiments, substantial purity entails a gold material, of which at least about 98% or higher, is pure gold. In other embodiments of the present invention, where the conductive fill is a fritted composite metal, glass, ceramic formulation, such metallizations are not required, but may improve conductivity and hermeticity.

Such filled or fritted embodiments entail, in some embodiments, a biocompatible composition, material, paste, epoxy, frit, fritting, conductive filling, conductive fill, conductive fritting, composite frits and/or fills, fritted metal composites, and the like, where such formulations have been modified to incorporate extra-constituent materials or components as a composite material. For example, but not limiting in any way, such filled or fritted materials include, one or more of a metal, glass fritted and/or filled materials, ceramic fritted and/or filled materials, and carbon fiber fritted and/or filled materials, biocompatible compositions, materials, and the like.

A variety of metal-containing compositions, e.g., pastes, inks, tapes, films, etc., are useful in forming electrically conductive pathways or passages with respect to the present feedthrough assemblies. Various techniques may be employed in order to electrically connect between two sides of a hermetic barrier, where, in some embodiments, the conductive fill not only imparts the conductive pathway, but it coterminous with the formation of the hermetic seal. These vias or openings are then filled with a conductive paste or fill. The conductive fill or paste serves to provide an electrical bridge or connection between the conductive layers. Because of its high electrical conductivity in concert with its functionality as a hermetic sealant, i.e., to a metallization layer, after sintering, gold, in a substantially pure form, e.g., 98% purity or higher, as a gold paste or solid gold body, is one of the preferred materials for forming the conductive pathway, while hermetically sealing the via hole.

Feedthrough assemblies disclosed herein, as shown in FIG. 2C in illustrative embodiments, have a ferrule 250 typically composed of an electrically conductive material, where the ferrule has an opening, and optionally a flange to facilitate direct contact with an insulator of the present disclosure. In some embodiments, the ferrule is configured to be attachable to an opening in a housing of a medical device. Likewise, the insulator at least partially residing in the ferrule opening, as shown in FIG. 2C, where a gold braze 251 hermetically seals the ferrule 250 to a metallized portion 252 of the insulator 210 in suitable embodiments.

In particular embodiments, moreover, the insulator possesses: (i) a thickness extending between an insulator first side and an insulator second side, (ii) a thick film membrane metallization residing at least partially on either or both of the insulator first side and the insulator second side to form a metallized insulator, and (iii) at least one via hole extending through the thickness of the metallized insulator. In certain embodiments, a fritted conductive fill is employed to reside at least partially within the at least one via hole, where, after sintering, the fritted conductive fill hermetically seals and forms a conductive pathway between the insulator first side and the insulator second side to form an electrically conductive hermetic via. In this respect, feedthrough assemblies of the present disclosure, in some embodiments, possess a leak rate of no greater than $1 \times 10^{-7}$ std cc He/sec. Various glass and ceramic fritted composites are known in the art. See, e.g., Smeacetto et al., "Glass and composite seals for the joining of YSZ to metallic interconnect in solid oxide fuel cells." Journal of the European Ceramic Society 28 (2008) 611-16.

The fritted conductive fills are selected from a glass-fritted metal body, a ceramic-fritted metal body, a glass and ceramic fritted metal body, and combinations thereof, while the fritted metal body also includes a metal selected from the group consisting of titanium, tantalum, niobium, gold, palladium, silver, molybdenum, and platinum, and combinations thereof. In some embodiments, at least one metal cover pad 331 conductively connected to the electrically conductive hermetic via, where the at least one metal cover pad 331 is disposed on either or both of the insulator first side and the insulator second side. In this respect, while the conductive fill, in some embodiments, constitutes the entirety of the conductivity with respect to the electrical pathway extending through the via hole, in other embodiments, a metal cover pad 331 increases the conductive surface area between the conductive via hole and the internal or external conductive device components.

Additionally or alternatively, an adhesion layer at least partially contacts either or both of the insulator first side and the insulator second side, and a wetting layer residing at least partially on the adhesion layer to form the external metallization. In certain embodiments, the conductive fills, fritted fills, pastes, composites, inks, compositions, formulations, and the like, of the present disclosure, further include one or more of a solvent, dispersant, viscosity modifier, binder, and the like.

Exemplary solvents to this end, include, but are not limited to, alcohols, such as methanol, ethanol, α-terpineol, and butylcarbitol acetate, methylethyl ketone, hydrocarbons, such as benzene and toluene, including mixtures thereof. The solvent is present to facilitate mixing and is subsequently removed either actively by heating or passively by evaporation during mixing, in certain embodiments. Also, α-terpineol and butylcarbitol acetate have relatively slow evaporation rates, and thus can also function as viscosity modifiers, in some embodiments.

Exemplary dispersants include, for example, but are not limited to, polymeric polyelectrolytes, such as those based on acrylic acid, including sodium and/or ammonium salts, e.g., NARLEX LD-42 and LD-45, available from National Starch Co., Bridgewater, N.J., and DARVAN C and 821A, available from R. T. Vanderbilt & Co., Norwalk, Conn., sodium, potassium, or ammonium polyphosphates and pyrophosphates, amines, such as di- or trialkylamines, e.g., eiethylamine, tripropylamine, di- or trialkanolamines, e.g., triethanolamine, N,N-diethyl-ethanolamine, polyethylene imines, e.g., Corcat P-600 (MW=600,000) and Corcat P-12 (MW=12,000), available from Virginia Chemical, Portsmouth, Va., morpholine, and other amine dispersants known in the art. Polyelectrolytes including quaternary ammonium salts, e.g., EMCOL CC-55 and CC-42, available from Witco Chem. Corp., Houston, Tex.; polyethylene glycols and polyoxyalkylene derivatives of propylene glycol, e.g., Pluronic L-12, available from BASF Corp., Parsippany, N.J., polyvinylpyrrolidone, vinylacetates, and the like, and compatible mixtures thereof, are also contemplated.

Exemplary viscosity modifiers include, but are not limited to, polyvinyl alcohol, cellulose derivatives, e.g., ethycellulose derivatives, methylcellulose, cellulose ethers such as that designated METHOCEL, available from Dow Chemical, Midland, Mi., glycols, e.g., polyethylene glycol and methoxypolyethylene glycol, e.g., Carbowax, available from Union Carbide, New York, N.Y., α-terpineol, butylcarbitol acetate (BCA), and the like, and mixtures thereof. Exemplary plasticizers are phthalate esters and mixtures thereof.

Ink and paste formulations are typically applied by a screen printing method. The viscosity of the formulation can be varied as desired, where, typically, trace inks have a lower viscosity and via inks have a higher viscosity, i.e., at least to maintain the applied ink or paste in the via hole. Solids loadings for the pastes and inks range from about 25-50% wt/vol., and, in some embodiments, from about 40-45% wt/vol. at lower loadings the sintered metallization becomes more porous, while at higher loadings, i.e., especially with respect to dense powders, providing an ink or paste that is easily printable becomes much more difficult. In general, the volume ratio of the non-volatile organics to the sinterable solids effects the green density of the metallization, which thereby effects the shrinkage upon sintering. For dense, co-fired vias, the non-volatile organics should be present in via inks at about 45% to 65% by volume, preferably 49.5% to 59.5%, most preferably 52% to 55%.

Binders, in some cases, should be used to keep the conductive fill, pastes, inks, and fritted-metal materials from disintegrating before firing. Binders that can be employed with respect to the present disclosure, either alone or in combination with other listed binders, include inorganic binders such as CERASET ceramer, and organic binders such as Acrawax, which is ethylene-bis steramide, ICI HYPERMERC) KD 2, and Dow XUS 40303 and 30303. Plasticizers such as Dow polyglycol E-400, and other known in the art, can be employed for particular applications. The mixture of conductive fill, dispersants, binder materials, plasticizers, etc., may be mixed with a solvent, such as ethanol or isopropanol, and/or additional materials know in the art, as needed.

One aspect of the present disclosure provides a flexible substrate assembly that entails: (i) an insulator having a thickness extending between an insulator first side and an insulator second side, (ii) at least one via hole extending through the thickness of the insulator, where the first via hole is provided with a via hole metallization residing at least partially on an internal surface of the at least one via hole to form at least one metallized via hole, and (iii) a conductive fill residing at least partially within the at least one metallized via hole, where the conductive fill hermetically seals and forms a conductive pathway between the insulator first side and the insulator second side to form an electrically conductive hermetic via.

The via hole metallization, in some embodiments, extends from the internal surface of the at least one via hole to at least a portion of either or both of the insulator first side and the insulator second side, where the conductive fill substantially covers the via hole metallization. Along the same lines, the flexible substrate assemblies provided herein include, in illustrative embodiments, an external or thick film metallization residing at least partially on either or both of the insulator first side and the insulator second side. In this respect, one or both of the via hole metallization and the external membrane metallization entail one or more materials selected from the group consisting of titanium, iridium, niobium, tantalum, ruthenium, zirconium, palladium, molybdenum, silver, platinum, copper, and carbon, and mixtures thereof.

The substrate insulators of the present disclosure include, in suitable embodiments, one or more layers of a material at least partially composed of zirconium oxide, sapphire, zirconia toughened alumina (ZTA), and yttria-stabilized-zirconia (YSZ). Such layers, in certain embodiments, possess a thickness ranging from about 1-50 µm. Inasmuch as the thin substrates impart characteristics required for miniature medical devices and feedthrough assemblies, the conductive via contact area, i.e., with respect to the electronic and body tissue contact, nevertheless requires supplication of at least one metal cover pad 331 conductively connected to the electrically conductive hermetic via, in some embodiments, where the at least one metal cover pad 331 is disposed on either or both of the insulator first side and the insulator second side.

Methods and Applications

In one aspect, the present disclosure is directed to a method of manufacturing a feedthrough assembly, which entails the steps of: (a) providing a ferrule composed of an electrically conductive material, the ferrule having a ferrule opening, where the ferrule is configured to be attachable to an opening in a housing of a medical device, (b) providing an insulator having a thickness extending between an insulator first side and an insulator second side, where the insulator is configured to at least partially reside in the ferrule opening, (c) introducing at least one via hole to the insulator, such that the at least one via hole extends through the thickness of the insulator, (d) providing at least one conductive filling to at least partially infiltrate the at least one via hole, and (e) subjecting the feedthrough assembly to at least one heating step to hermetically seal and form a conductive pathway between the insulator first side and the insulator second side, where the at least one heating step separately, sequentially, or simultaneously, forms a hermetic connection between the ferrule and the insulator.

The conductive filling, in some embodiments, includes one or more of a via hole metallization, a fritted metal paste, a substantially pure metal paste, and a substantially pure metal body, and combinations thereof. The fritted metal paste, substantially pure metal paste, and a substantially pure metal body, in this regard, are at least partially formulated with a metal selected from titanium, tantalum, niobium, gold, palladium, silver, molybdenum, and platinum, and combinations thereof. The methods of the present disclosure further include, in illustrative embodiments, the step of providing an external metallization to the insulator after the step of the substrate insulator is provided, but prior to the via hole introduction, to ultimately form a metallized insulator. In accord, the external metallization at least partially resides on either or both of the insulator first side and the insulator second side as a membrane-bound metallization.

A via hole metallization at least partially residing within at least one via hole is provided, in suitable embodiments, prior to or after the insulator is sintered. Simply put, forming and sintering the substrate prior to, for example, the application of laser drilling to introduce the via holes into the substrate occurs in some embodiments, while other embodiments entail the formation of the via holes within the green body, followed by sintering the insulator to a brown state. In either case, via hole metallization cannot precede via hole formation, i.e., to the extent that via hole metallization is being performed.

Via hole metallization includes the application of an adhesion layer to the internal surface of the via hole, followed by the introduction of a wetting layer on the adhesion layer, in illustrative embodiments. In some embodiments, the metallization is composed of one or more metals selected from niobium, molybdenum, palladium, and platinum, and mixtures thereof. In certain embodiments, the adhesion layer is titanium, and the wetting layer is niobium and/or molybdenum.

The present methods further entail the step of sintering one or more layers of a material selected from the group consisting of yttria-stabilized-zirconia (YSZ), e.g., 3YSZ, zirconium oxide, sapphire, and zirconia toughened alumina (ZTA), and mixtures thereof, where the insulator is in a green state. In some embodiments, the insulator substrate is provided by performing a tape casting process to form one or more layers of an insulator substrate. The methods further include the formation of one or more counterbores at least partially within the at least one via hole on either or both of the insulator first side and the insulator second side of the insulator body.

Forming or introducing at least one via hole, with or without establishing a counterbore therein, proceeds such that the via hole extends through the thickness of the insulator, where, in some embodiments, laser drilling, punching, machining, extrusion, or waterjet cutting is employed to introduce the via holes into the insulator body. Likewise, certain embodiments include, single or multiple via holes that are introduced into the substrate either in a repeating array pattern or a random pattern, using various hole forming methods, such as, but not limited to, laser cutting, laser machining, mechanical drilling, reactive-ion etching, ion-milling, deep reactive ion etching, water-jet cutting, or wet etching, ultrasonic drilling, and combinations thereof.

The conductive filling is applied to at least one via hole and/or at least metallized via hole, in some embodiments, to at least partially infiltrate the at least one via hole. In some embodiments the conductive filling is a paste, powder, slurry, epoxy, ink, solid sheet, preform, or other form of conductive formulation to be applied to a via hole or metallized via hole, and pluralities thereof. In this respect, the conductive filling is composed from an electrically conductive powder, in some embodiments, which included, but are not limited to, one or more carbon powders and metal powders, such as copper, silver, nickel, molybdenum, gold, palladium, platinum, aluminum powder and mixtures thereof, each having an average particle size of about 0.1 to about 10 microns, in some embodiments.

Illustrative embodiments of the present invention entail thick-film process application, thin-film process application, injection molding, screen printing, overplating, application of sacrificial layers or coatings, sputtering, vacuum pulling, extrusion techniques, CVD, and other known techniques in the art for the application and subsequent infiltration into the via hole or metallized via hole of the conductive filling. In turn, the conductively filled via holes are then subjected to at least one heating step to hermetically seal and form a conductive pathway between the insulator first side and the insulator second side, where the at least one heating step separately, sequentially, or simultaneously, forms a hermetic connection between the ferrule and the insulator.

The heating step, in this regard, establishes a bonding interaction between the conductive filling and the metallized via hole or the insulator substrate in embodiments that do not include via hole metallization. Bond formation between the insulator and ferrule are similarly formed pursuant to the heating, which ultimately imparts hermeticity to the entire feedthrough assemblies disclosed herein. In illustrative embodiments, the bond formation occurs pursuant to heating the insulator, which accordingly, precipitates evaporation, binder burnout, sintering, etc.

In accord, areas lacking via holes, e.g., any unpunched ceramic layers, nevertheless facilitate constraint of the conductive paste within via holes and accordingly allow for compression during the heating. In illustrative embodiments, an exemplary heating step, includes, but is not limited to, a ramping stage up to 600° C. at a rate of about 1° C./minute, then increasing the temperature to 1100° C. at a rate of about 5° C./minute, followed by a one hour dwell and subsequent cool-down phase. During the heating and subsequent cooling, the insulator contracts thereby conforming the via holes around the conductive filling, e.g., the gold paste, to form a hermetic seal.

At the peak temperature, e.g., 1100° C., the conductive filling exhibits sufficient flow to enable the, for example, substantially gold paste, to flow and fill any crevices in the ceramic. This infiltration accordingly produces a hermetic seal between the conductive filling and the ceramic, or metallized ceramic, interface within the via holes, including bonding interactions that occur on the insulator first side and second side with respect to the conductive fill. Furthermore, the heating step may also impart hermeticity through bonding mechanisms like, for example, sintering, glass melt/ wetting, alloying, compounding and/or diffusion solution formation.

Following the heating step the substrate assemblies are grinded and polished, in some embodiments, to a surface roughness, ranging from about 25-50 nm Ra. In some embodiments, the surface roughness ranges from about 0.01, 0.1, 1, 0.25, 0.5, 0.75, 1, 3, 5, 7, 9, 10, 15, 20, 30, 50, 100, 500, or 900 nm Ra to from about 0.1, 0.25, 0.5, 0.75, 1, 3, 5, 7, 9, 10, 15, 20, 30, 50, 100, 500, or 900 nm Ra.

The present disclosure is not to be limited in terms of the particular embodiments described in this application. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

All references cited herein are incorporated by reference herein in their entireties and for all purposes to the same extent as if each individual publication, patent, or patent application was specifically and individually incorporated by reference in its entirety for all purposes.

What is claimed is:

1. A feedthrough assembly, comprising:
    a) a ferrule comprising an electrically conductive material, the ferrule comprising a ferrule opening, wherein the ferrule is configured to be attachable to an opening in a housing of a medical device;
    b) an insulator at least partially residing in the ferrule opening where a gold braze hermetically seals the insulator to the ferrule, wherein the insulator has a thickness extending to an insulator first side and an insulator second side with at least one via hole extending through the thickness of the insulator;
    c) a via hole metallization residing in the via hole to thereby form an at least one metallized via hole, wherein the via hole metallization extends to a via hole metallization extended portion residing on at least one of the insulator first and second sides; and
    d) an electrically conductive material residing in the at least one metallized via hole and being hermetically sealed to the via hole metallization to thereby form a hermetic and electrically conductive pathway extending to the insulator first and second sides.

2. The feedthrough assembly of claim 1, wherein the electrically conductive material is substantially pure gold.

3. The feedthrough assembly of claim 1, wherein an adhesion layer contacts an internal surface of the at least one via hole, and a wetting layer resides at least partially on the adhesion layer to form the via hole metallization of the at least one metallized via hole.

4. The feedthrough assembly of claim 3, wherein the wetting layer contacts the electrically conductive material to form the hermetic and electrically conductive pathway.

5. The feedthrough assembly of claim 1, wherein the via hole metallization comprises one or more materials selected from the group of titanium, iridium, niobium, tantalum, ruthenium, zirconium, palladium, molybdenum, silver, platinum, copper, carbon, and mixtures thereof.

6. The feedthrough assembly of claim 1, wherein the insulator comprises one or more layers of a material at least partially composed of zirconium oxide, sapphire, zirconia toughened alumina (ZTA), yttria-stabilized-zirconia (YSZ), and 3 mol % yttria-stabilized-zirconia (3YSZ).

7. The feedthrough assembly of claim 1, wherein an electrically conductive material overlay portion substantially covers the via hole metallization extended portion residing on the at least one of the insulator first and second sides.

8. The feedthrough assembly of claim 1, wherein the thickness of the insulator is from about 20 µm to about 40 µm.

9. The feedthrough assembly of claim 7, further comprising at least one metal cover pad conductively connected to the electrically conductive material overlay portion residing on the at least one of the insulator first and second sides.

10. The feedthrough assembly of claim 1, wherein the via hole metallization extended portion comprises a via hole metallization first extended portion residing on the insulator first side and a via hole metallization second extended portion residing on the insulator second side, and wherein the electrically conductive material comprises an electrically conductive material first overlay portion substantially overlaying the via hole metallization first extended portion and an electrically conductive material second overlay portion substantially overlaying the via hole metallization second extended portion, the electrically conductive material first and second overlay portions being continuous with the electrically conductive material residing in the at least one metallized via hole.

11. The feedthrough assembly of claim 1, wherein the electrically conductive material extends to an electrically conductive material third overlay portion directly contacting at least one of the insulator first and second sides.

12. The feedthrough assembly of claim 1, wherein the electrically conductive material comprises an electrically conductive material first overlay portion directly contacting the insulator first side and an electrically conductive material second overlay portion directly contacting the insulator second side, the electrically conductive material first and second overlay portions being continuous with the electrically conductive material residing in the at least one metallized via hole.

13. The feedthrough assembly of claim 1, wherein the at least one via hole has a first diameter and the via hole metallization extended portion has a second diameter, and wherein the second diameter is about 2 to 5 times greater than the first diameter.

14. The feedthrough assembly of claim 1,
  i) wherein the ferrule is configured to be attached to a metal housing of an implantable medical device, and
  ii) wherein the at least one via hole extends through the insulator to an insulator external device side end surface at the insulator first side opposite an insulator internal device side end surface at the insulator second side, and
  iii) wherein, when the ferrule hermetically sealed to the insulator is attached to the AIMD housing, the insulator external device side end surface and the insulator internal device side end surface reside outside and inside the implantable device housing, respectively.

15. The feedthrough assembly of claim 1, wherein the at least one via hole has a taper providing a larger open diameter at the insulator first side than at the insulator second side.

16. The feedthrough assembly of claim 1, being configured for connection to an implantable medical device selected from the group of a pacemaker, a cardioverter-defibrillator, a neurostimulator, a drug pump, a ventricular assist device, a nerve stimulator, a brain stimulator, an organ stimulator, a muscle stimulator, a monitor, a sensor, a cardiac contractility modulator, a drug administering device, a diagnostic recorder, and a cochlear implant.

17. A flexible substrate comprising:
  a) an insulator having a thickness extending to an insulator first side and an insulator second side;
  b) at least one via hole extending through the thickness of the insulator;
  c) a via hole metallization residing at least partially on an internal surface of the at least one via hole to form at least one metallized via hole, wherein the via hole metallization extends to a via hole metallization extended portion residing on at least one of the insulator first and second sides; and
  d) an electrically conductive material residing in the at least one metallized via hole and being sealed to the via hole metallization to thereby form a hermetic and electrically conductive pathway extending to the insulator first and second sides.

18. The flexible substrate of claim 17, wherein the electrically conductive material comprises an electrically conductive material overlay portion that substantially covers the via hole metallization extended portion residing on the at least one of the insulator first and second sides.

19. The flexible substrate of claim 17, wherein the electrically conductive material is substantially pure gold.

20. The flexible substrate of claim 17, wherein the via hole metallization comprises one or more materials selected from the group of titanium, iridium, niobium, tantalum, ruthenium, zirconium, palladium, molybdenum, silver, platinum, copper, and carbon, and mixtures thereof.

21. The flexible substrate of claim 17, wherein the insulator comprises one or more layers of a material at least partially composed of zirconium oxide, sapphire, zirconia toughened alumina (ZTA), yttria-stabilized-zirconia (YSZ), and 3 mol % yttria-stabilized-zirconia (3YSZ).

22. The flexible insulator substrate of claim 17, being configured for incorporation into an implantable medical device selected from the group of a pacemaker, a cardioverter-defibrillator, a neurostimulator, a drug pump, a ventricular assist device, a nerve stimulator, a brain stimulator, an organ stimulator, a muscle stimulator, a monitor, a sensor, a cardiac contractility modulator, a drug administering device, a diagnostic recorder, and a cochlear implant.

23. The flexible substrate of claim 17, wherein the thickness of the insulator is from about 5 µm to about 50 µm.

24. A method for manufacturing a feedthrough assembly, the method comprising the steps of:
  a) providing a ferrule composed of an electrically conductive material, the ferrule comprising a ferrule opening, wherein the ferrule is configured to be attachable to an opening in a housing of a medical device;
  b) providing an insulator having a thickness extending to an insulator first side and an insulator second side, wherein the insulator is configured to at least partially reside in the ferrule opening;
  c) introducing at least one via hole extending through the thickness of the insulator;

d) metallizing the via hole with a via hole metallization to form at least one metallized via hole, wherein the via hole metallization extends to a via hole metallization extended portion formed separately, sequentially, or simultaneously with the via hole metallization and residing on at least one of the insulator first and second sides;

e) providing an electrically conductive material in the at least one metallized via hole; and f) subjecting the feedthrough assembly to at least one heating step to hermetically seal the electrically conductive material to the via hole metallization and form a hermetic and electrically conductive pathway extending to the insulator first and second sides, and g) wherein the at least one heating step separately, sequentially, or simultaneously forms a hermetic connection between the ferrule and the insulator.

25. The method of claim 24, including providing the electrically conductive material comprising one or more of a fritted metal paste, a substantially pure metal paste, and a substantially pure metal.

26. The method of claim 25, including providing the fritted metal paste, the substantially pure metal paste, and the substantially pure metal comprising a metal selected from the group of titanium, tantalum, niobium, gold, palladium, silver, molybdenum, and platinum, and combinations thereof.

27. The method of claim 24, further comprising the step of providing a thick film metallization to the insulator after step b) and prior to step c) to form a metallized insulator, wherein the thick film metallization at least partially resides on either or both of the insulator first side and the insulator second side.

28. The method of claim 24, further comprising sintering the insulator after the step c) introducing.

29. The method of claim 24, including providing the electrically conductive material comprising an electrically conductive material overlay portion substantially covering the via hole metallization extended portion on the at least one of the insulator first and second sides.

30. The method of claim 24, including providing the via hole metallization comprising a via hole metallization first extended portion residing on the insulator first side and a via hole metallization second extended portion residing on the insulator second side, and further providing the electrically conductive material comprising an electrically conductive material first overlay portion substantially overlaying the via hole metallization first extended portion, and an electrically conductive material second overlay portion substantially overlaying the via hole metallization second extended portion, the electrically conductive material first and second overlay portions being continuous with the electrically conductive material in the at least one metallized via hole.

31. The method of claim 30, including providing the electrically conductive material extending to an electrically conductive material third overlay portion directly contacting at least one of the insulator first and second sides.

32. A flexible substrate, comprising:
   a) an insulator having a thickness extending to an insulator first side and an insulator second side with at least one via hole extending through the thickness of the insulator;
   b) a via hole metallization residing in the via hole to thereby form an at least one metallized via hole; and
   c) an electrically conductive material residing in the at least one metallized via hole and being hermetically sealed to the via hole metallization to thereby form a hermetic and electrically conductive pathway extending to the insulator first and second sides,
   d) wherein the electrically conductive material comprises an electrically conductive material first overlay portion directly contacting the insulator first side and an electrically conductive material second overlay portion directly contacting the insulator second side, the electrically conductive material first and second overlay portions being continuous with the electrically conductive material in the at least one metallized via hole.

33. The flexible substrate of claim 32, wherein the thickness of the insulator is from about 5 µm to about 50 µm.

* * * * *